United States Patent [19]

Longo et al.

[11] Patent Number: 4,871,716

[45] Date of Patent: * Oct. 3, 1989

[54] MAGNETICALLY RESPONSIVE, HYDROPHILIC MICROSPHERES FOR INCORPORATION OF THERAPEUTIC SUBSTANCES AND METHODS OF PREPARATION THEREOF

[75] Inventors: William E. Longo; Richard A. McCluskey; Eugene P. Goldberg, all of Gainesville, Fla.

[73] Assignee: University of Florida, Gainesville, Fla.

[*] Notice: The portion of the term of this patent subsequent to Jun. 9, 2004 has been disclaimed.

[21] Appl. No.: 937,611

[22] Filed: Dec. 3, 1986

Related U.S. Application Data

[63] Continuation-in-part of Ser. No. 825,789, Feb. 4, 1986, Pat. No. 4,671,954, which is a continuation of Ser. No. 560,952, Dec. 13, 1983, abandoned.

[51] Int. Cl.$^4$ .................... A61K 37/02; A61K 33/26
[52] U.S. Cl. .................................. 514/2; 106/124; 252/62.51; 252/62.55; 424/9; 424/491; 424/497; 424/499; 424/501; 436/526; 436/528; 436/531; 436/829; 435/7; 514/6

[58] Field of Search ............... 436/526, 528, 531, 829; 424/9, 491, 497, 499, 501; 435/7; 514/2, 6; 252/62.51, 62.55; 106/124

[56] References Cited

U.S. PATENT DOCUMENTS

| | | | |
|---|---|---|---|
| 4,157,323 | 6/1979 | Yen et al. | 436/526 |
| 4,169,804 | 10/1979 | Yapel, Jr. | 436/526 |
| 4,671,954 | 6/1987 | Goldberg et al. | 436/829 |
| 4,695,393 | 9/1987 | Whitehead et al. | 436/526 |

OTHER PUBLICATIONS

Longo et al., "Preparation of Hydrophilic Albumin Microspheres Using Polymeric Dispersing Agents" J. Pharm. Sci. 71 (2), Dec. 1982: 1323–1328.

*Primary Examiner*—Christine M. Nucker
*Attorney, Agent, or Firm*—Dennis P. Clarke

[57] ABSTRACT

Novel magnetically responsive hydrophilic protein or polypeptide microspheres prepared by dispersing an aqueous solution or dispersion of protein or polypeptide and particulate magnetically responsive material in an organic solvent solution of a high molecular weight polymer to form a stabilized dispersion of microspheres and cross-linking said microspheres with a polyfunctional cross-linking agent.

33 Claims, No Drawings

4,871,716

MAGNETICALLY RESPONSIVE, HYDROPHILIC MICROSPHERES FOR INCORPORATION OF THERAPEUTIC SUBSTANCES AND METHODS OF PREPARATION THEREOF

This is a CIP of application Ser. No. 825,789, filed Feb. 4, 1986, and now U.S. Pat. No. 4,671,954; which is a continuation of Ser. No. 560,952, filed Dec. 13, 1983, abandoned.

BACKGROUND OF THE INVENTION

Insoluble magnetically responsive polypeptide or protein microspheres containing therapeutic agents that enable the controlled releases thereof in biological systems following localization by an externally applied magnetic field have generated growing interest in recent years [Widder et al: Cancer Research, 40, p. 3512 (1980) and Widder et al: J. Pharm. Sci., 68, p. 79 (1979)]. Systems utilizing the microspheres have the potential advantage of prolonging effective drug concentrations in the blood stream or tissue when injected thereby reducing the frequency of administration; localizing high drug concentrations; reducing drug toxicity, and enhancing drug stability. Albumin is a preferred protein or polypeptide for the preparation of such microspheres since it is a naturally occurring product in human serum. Although it is usually necessary to cross-link the albumin when preparing microspheres according to conventional methods, cross-linked albumin may still be degraded depending upon cross-link density thereby enabling the use thereof for drug delivery systems, etc.

Conventional methods for the preparation of magnetically responsive albumin microspheres are generally of two types. In one method, aqueous dispersions of albumin and magnetically responsive material are insolubilized in vegetable oil or isooctane or other hydrocarbon solvent by denaturing at elevated temperatures (110°–165° C.). Another method involves chemical cross-linking of the aqueous dispersion of albumin at room temperature. Typical of these two types of methods are those described in U.S. Pat. Nos. 4,147,767; 4,356,259; 4,349,530; 4,169,804; 4,230,687; 3,937,668; 3,137,631; 3,202,731; 3,429,827; 3,663,685; 3,663,686; 3,663,687; 3,758,678 and Ishizaka et al, J. Pharm. Sci., Vol. 20, p. 358 (1981). See also U.S. Pat. Nos. 4,055,377; 4,115,534; 4,157,323; 4,169,804; 4,206,094; 4,218,430; 4,219,411; 4,247,406; 4,331,654; 4,345,588; 4,369,226; and 4,454,234.

These methods, however, result in the formation of relatively hydrophobic microspheres which usually require a surfactant in order to disperse a sufficient quantity thereof in water or other systems for administration to a biological system to ensure the delivery thereto of an effective amount of any biologically active agent entrapped therein. In addition, the hydrophobic nature of conventional polypeptide microspheres make it difficult to "load" large quantites of some water soluble biologically active agents or other material within the microspheres after synthesis.

It is an object of the present invention to provide more hydrophilic magnetically responsive polypeptide microspheres which will accept high "loadings" of biologically active substances of other materials especially by addition of such substances after microsphere synthesis, and to prepare such drug loaded microspheres which do not require the utilization of surfactants to enable the preparation of highly concentrated dispersions thereof.

It is a further object of the invention to provide hydrophilic magnetically responsive microspheres which may be more readily modified by aqueous chemical methods to covalently attach proteins, enzymes, antibodies, immunostimulants, and other compounds to alter and improve microsphere properties.

It is a further object of the present invention to provide a novel method for the preparation of such magnetically responsive hydrophilic microspheres.

It is still a further object of the present invention to provide novel hydrophilic microspheres containing biologically active or other substances and a method for the preparation thereof.

It is still a further object of the present invention to provide a composition for administration to an animal, including humans, comprising novel hydrophilic, magnetically responsive polypeptide microspheres containing a biologically active substance.

It is still a further object of the present invention to provide a novel method for administering a biologically active substance to an animal based upon a system comprising hydrophilic, magnetically responsive polypeptide microspheres containing a biologically active substance.

SUMMARY OF THE INVENTION

The foregoing and other objects of the invention are provided by novel hydrophilic, magnetically responsive microspheres prepared by a method comprising (a) providing a dispersion of an aqueous solution or dispersion of polypeptide or protein microspheres and a particulate magnetically responsive material in an organic substantially water immiscible solvent solution of high molecular weight polymer wherein the organic solvent is substantially a non-solvent for the protein microspheres and the soluble polymer stabilizes the magnetically responsive protein or polypeptide microsphere dispersion.

(b) incorporating a polyfunctional cross-linking agent for the protein or polypeptide in the dispersion, and (c) allowing the cross-linking agent to react with the protein or polypeptide microspheres for a time sufficient to cross-link at least a portion of the microspheres and, thereby to render the microspheres substantially insoluble in water and to provide free reactive functional groups therein.

The present invention also provides novel cross-linked hydrophilic, magnetically responsive polypeptide microspheres containing additional substances prepared by reacting the free reactive functional groups of the above-described cross-linked protein microspheres with substances containing at least one functional group reactive therewith to form a covalent or other type of bond between the cross-linked protein microspheres and the additional substance.

The present invention provides compositions for administration to biological systems comprising biologically effective amounts of the above-described cross-linked hydrophilic, magnetically responsive polypeptide microspheres bonded with a biologically active substance.

The present invention also provides a method of administering a biologically active substance to a biological system comprising administering thereto a biologically effective amount of the above-described composition.

DETAILED DESCRIPTION OF THE INVENTION

The present invention is predicated on the discovery that more hydrophilic, magnetically responsive protein or polypeptide microspheres can be prepared than heretofore if an aqueous solution or dispersion of polypeptide or protein and magnetically responsive material polypeptide or protein solution is first dispersed in organic solvent solutions of certain high molecular weight polymers wherein the organic solvent is a non-solvent for the aqueous polypeptide. The resulting dispersion comprises a polypeptide or protein solution and magnetically responsive material dispersed in a high molecular weight polymer solution in an organic solvent external phase. This polymer solution functions to stabilize the aqueous magnetically responsive protein or polypeptide dispersion and ensures the integrity of the individual microspheres.

When a polyfunctional cross-linking agent is introduced into this dispersion, preferably in the form of an organic solvent solution, the cross-linking agent is presented initially to the external surfaces of the microspheres rather than to the interior thereof as in the conventional prior art methods for microsphere production, thereby creating a relatively higher cross-link density at the surfaces of the microspheres than in the interior. This phenomenon also gives rise to a high concentration of free reactive functional groups from the cross-linking agent at the surface of the microspheres thereby facilitating increased hydrophilicity thereof especially if the microspheres are allowed to react with an added reagent reactive therewith, e.g., an amino acid or amino alcohol. The availability of these free amino acid or amino alcohol functional groups for reaction with other substances containing functional groups reactive therewith also renders the microspheres capable of being much more highly "loaded", i.e., up to about 50% by weight, with additional substances such as therapeutically active agents, etc., than conventional microspheres.

Moreover, the more hydrophilic nature of the microspheres enhances their dispersion in aqueous media, thereby enabling the safe administration thereof to animals, including humans, or other biological systems in much greater amounts than conventional hydrophobic microspheres, which require the presence of possibly biologically deleterious amounts of surfactants to achieve similar concentrations of administrable microspheres.

It will be understood by those skilled in the art, having been exposed to the principles of the present invention, that any protein or polypeptide capable of forming a cross-linked microsphere may be employed in the practice of the invention. Suitable such proteins or polypeptides include serum albumin, poly-L-lysine, poly-L-arginine, poly-L-histidine, polyglutamic acid, and any water soluble protein with functional amine groups such as enzymes, immunoglobulins, etc.

Furthermore, other polypeptides or macromolecules may be incorporated into the albumin microspheres even if they do not participate in the cross-linking reaction. These may be added to the albumin in the aqueous phase in concentrations ranging from 0.1 to 30%, by weight, or more and become entrapped during the cross-linking process. Such added macromolecules include, for example, polyglutamic acid, carboxymethyl dextran, carboxymethyl cellulose, polygalacturonic acid, cellulose, dextran, etc.

Where the microspheres are to be subsequently reacted with a biologically active substance to produce a composition suitable for administration to a biological system, it is preferred to utilize an albumin to form the microsphere since it is a naturally occurring substance in most biological systems. Moreover, albumin, which has been cross-linked with most polyfunctional reagents, may be degraded, in vivo, depending upon the extent of cross-linking, after administration to a biological system. Although any form of albumin may be used in the practice of the invention, it is preferred to match the albumin with the biological system to which microspheres prepared therefrom are administered, e.g., human serum albumin, bovine serum albumin, rabbit serum albumin, fatty acid free human serum albumin, dog serum albumin, egg albumin, horse serum albumin, etc.

The aqueous solution or dispersion of protein or polypeptide is first dispersed in an organic solvent solution of a high molecular weight polymer.

Any polymer capable of forming a stabilized dispersion of the protein or polypeptide may be utilized in the practice of the invention. The polymer solution should be one which stabilizes the resulting dispersion of microspheres in the organic solvent/aqueous external phase against coagulation, agglomeration, etc. Suitable such polymers include, for example, acrylic polymers, e.g., polymethylmethacrylate, etc., polyoxyethylenepolyoxypropylene block copolymers, cellulose acetatebutyrate, polycarbonates, e.g., bisphenol polycarbonate, etc., polysulfones, polyacrylamides, polyvinyl alcohols, polyacetals, polystyrene and copolymers thereof, polyesters, polyamides, etc.

The organic solvent for the polymer should be a non-solvent for the aqueous protein or polypeptide solution and inert with respect thereto and capable of forming at least a 1–40%, by weight, solution of the polymer. Suitable solvents will depend, of course, upon the particular protein or polypeptide used to form the microspheres and the stabilizing polymer. Having been exposed to the principles of the present invention those skilled in the art will be able to determine suitable polymers and organic solvents without the exercise of inventive faculties or undue experimentation. Typical of useful organic polymer solvents are toluene, benzene, chloroform, ethylene dichloride, methylene chloride, etc., and mixtures thereof.

By the term "magnetically responsive material" is meant any magnetic or magnetizable material such as Fe, Ni, Co or alloys thereof; metal oxides such as magnetite ($Fe_3O_4$), $BaFe_{12}O_{19}$, CoO, NiO, $Mn_2O_3$ and other ferromagnetic materials such as CoMnP.

The magnetically responsive material is preferably dispersed in the albumin solution or dispersion in particulate form, i.e., having a particle size in the range of from about 50 angstroms to about 500 angstroms.

The term "microsphere" is intended to include any small particles of protein or polypeptide or mixture thereof with other macromolecules of generally spherical shape which is formed upon dispersion of an aqueous solution of protein or polypeptide in an organic solvent solution of a stabilizing polymer.

The stabilization of the microspheres is largely dependent upon the concentration and molecular weight (M.W.) of the polymer in the organic solvent. Generally, as the M.W. of the polymer is increased, the concentration of said polymer can be decreased. The upper limit of polymer concentration is governed by the ease of removal of the polymer after microsphere cross-linking. Generally, concentrations between about 1% and 30%, by weight, depending upon the particular protein or polypeptide and polymer selected, will be sufficient to produce suitable dispersions.

Average size and size distribution of the microspheres is usually a function of the shear forces and the time, i.e., energy, necessary to prepare the dispersions. Increasing either the shear forces or time of dispersion or both decreases the size of the microspheres. Generally, when producing large microspheres, a lower polymer concentration may be used. Smaller microspheres may require either a low or higher polymer concentrations depending on the type of polymer used and more dilute protein dispersions.

Microspheres having a size in the range of from about 0.05 micron to about 500 microns may be prepared according to the method of the invention. Those skilled in the art having been exposed to the principles of the invention as described herein will be capable of selecting appropriate polymer concentrations and molecular weights and dispersion techniques to prepare microspheres of a desired size without the exercise of inventive faculties and undue experimentation.

Suitable cross-linking agents include polyfunctional reagents capable of reacting with the functional groups, particularly the amino groups, present on the protein or polypeptide to cross-link the molecules thereof. The selection of a particular cross-linking agent will depend to a large extent upon the intended use of the microspheres. Generally, however, any polyfunctional reagent, including those used heretofore in prior art methods to cross-link proteins, may be utilized to form the microspheres of the present invention. Typical of such reagents are polyaldehydes such as glutaraldehyde and polyisocyanates such as 2,4-tolylenediisocyanate, 1,6-diisocyanatohexane and activated polyfluoro compounds such as 1,5-difluoro-2,4-dinitrobenzene and P,P'-difluoro-m,m'-dinitrodiphenylsulfone.

The cross-linking agent is preferably presented to the microspheres by incorporating in the above-described dispersion of protein or polypeptide microspheres an organic solvent solution of the cross-linking agent. The organic solvent for the cross-linking agent is one that is compatible with the solvent for the organic polymer and is likewise a non-solvent for the microspheres. The cross-linker diffuses into the microspheres from the organic phase with consequent increased concentration at the surfaces thereof. As a result, the outer surfaces of the microspheres are usually cross-linked to a greater extent than the interior portions.

This is in contrast to conventional prior art methods wherein the cross-linker is usually present in the aqueous protein dispersion thereby resulting in substantially uniform cross-linking throughout the microspheres. In addition, there is a larger concentration of free functional groups at the outer surfaces of the microspheres of the present invention as a result of some reactions between only one of the functional groups of the cross-linker with amino groups of protein or polypeptide molecules. However, if so desired, the cross-linking agent could be added to the microspheres according to the conventional method.

These free reactive functional groups (e.g., aldehyde groups, where the cross-linker is a polyaldehyde) at the surface render the microspheres more hydrophilic and readily susceptible to wetting and dispersion in aqueous media, especially when further reacted with polar compounds such as amino acids or amino alcohols or when oxidized to carboxylic groups.

Suitable organic solvents for the cross-linking agent include any which are non-solvents for the microspheres and which are compatible with the solvent for the organic polymer and the cross-linking agent. Suitable solvents include those listed above as suitable for solubilizing the polymer. Those skilled in the art, having been exposed to the principles of the present invention, will be capable of selecting suitable solvents for the cross-linkers without the exercise of inventive faculties or undue experimentation.

The cross-link density as well as the number of free functional groups at the surfaces of the microspheres can be controlled by regulating the concentrations of the cross-linking agent. Generally, as the concentration of cross-linker in the final dispersion is increased, the cross-link density and the number of free functional groups at the outer surfaces of the microspheres are increased. For most applications, a sufficient quantity of cross-linker solution is added to the microsphere dispersion to yield a final cross-linker concentration therein of between about 0.1% and about 25%, by weight. It will be understood, however, that any concentration consistent with an efficient completion of the method and the intended use of the microspheres may be utilized.

The following non-limiting examples are illustrative of the novel microspheres of the present invention and of methods for their preparation and use.

Preparation of glutaraldehyde cross-linked human serum albumin(HSA) microspheres(MS)

EXAMPLE 1

HSA (0.150 g) (Sigma, recrystallized and lyophilized) was dissolved in 0.5 ml water in a 16×125 mm test tube (this size test tube was used throughout all of the following procedures except where noted). The solution was added drop wise to a 25 wt % solution of polymethylmethacrylate (PMMA) (Polyscience, intrinsic viscosity 1.4) in a mixture of 1.5 ml chloroform and 1.5 ml toluene in a screw cap test tube. The mixture was dispersed with a vortex mixer (Vortex Genie Scientific Industries, Inc.) for two minutes at a power setting of nine. Aqueous glutaraldehyde 1.0 ml (25 wt %) and 1.0 ml of toluene were combined in a 13×100 mm test tube. The two phases were dispersed by ultrasonification (Heat Systems-Ultrasonics, Model W-375) with a microtip power head attachment (20 secs. at 50 watts). The resulting toluene solution of glutaraldehyde, (0.14 mmoles) was allowed to phase separate, pipeted off, and combined with the albumin dispersion. After addition of the glutaraldehyde saturated toluene, the albumin dispersion was mixed with a rotary mixer (Labquate Labindustries) at room temperature (r.t.) for 8 hrs. The resulting cross-linked HSA/MS were washed to remove all PMMA dispersant by the addition of 10.0 ml of acetone, test tube briefly agitated, then centrifuged (2000 RPM×2 min.), the supernate discarded and the HSA/MS-U pellet re-suspended with an additional 10.0 ml of acetone. This wash procedure was repeated eight times. After the last wash, HSA/MS were allowed to air dry. The product was a brown powder, 0.122 g, 81% yield. The average diameter of the HSA/MS was 29 μm as determined by optical microscopy.

EXAMPLE 2

HSA (0.150 g) was dissolved in 0.5 ml of water in a test tube. This solution was added dropwise to a 25 wt % solution of polyoxyethylene/polyoxypropylene copolymer (Poloxmer 188 (BASF Wandotte Corp., MW 8430)) in 4.0 ml chloroform in a screw cap test tube. The mixture was dispersed with a vortex mixer for two minutes at power setting nine. Glutaraldehyde was used for cross-linking and was prepared with chloroform by sonification as previously described in Example 1. After addition of the glutaraldehyde saturated chloroform, the albumin dispersion was mixed with a rotary mixer at r.t. for 6 hrs. The resulting cross-linked HSA/MS were washed to remove all Poloxmer 188 dispersant as described in Example 1. The MS product was a brown powder, 0.115 g, 77% yield. The average diameter was 20–40 $\mu$m, as determined by optical microscopy.

EXAMPLE 3

HSA (0.150 g) was dissolved in 0.5 ml of water in a test tube. This solution was added dropwise to a 3.0 wt % solution of cellulose acetate butyrate (CAB Polyscience, MW 73,000) in 4.0 ml of ethylene dichloride in a screw cap test tube. The mixture was dispersed with a vortex mixer for two minutes at power setting nine. Glutaraldehyde was used for cross-linking and was prepared as described in Example 1. After addition of the glutaraldehyde saturated toluene, the dispersion was mixed with a rotary mixer at r.t. for 24 hrs. The resulting cross-linked HSA/MS were washed to remove all CAB dispersant and dehydrated as described in Example 1. The MS product was a brown powder, 0.11 g, 73% yield. The average diameter was 25 $\mu$m determined by optical microscopy.

EXAMPLE 4

HSA (0.156 g) was dissolved in 0.5 ml of water in a test tube. This solution was added dropwise to a 20 wt % solution of bisphenyl polycarbonate (General Electric, MW 32,000) in 4.0 ml of chloroform. Glutaraldehyde was used for cross-linking and was prepared as described in Example 2. After addition of the glutaraldehyde saturated chloroform, the mixture was mixed with a rotary mixer at r.t. for 16 hrs. The resulting cross-linked HSA/MS were washed to remove all polycarbonate dispersant by the addition of chloroform (8 X, 10.0 ml volumes), then acetone (8 X, 10.0 ml volumes) and water (4 X, 5.0 ml volumes). After the water wash, MS were examined with an optical microscope and stored frozen at 0° C. Average diameter of the MS were 10–50 $\mu$m.

EXAMPLE 5

Human Serum Albumin (Fatty Acid Free (FAF) Microspheres-Unquenched

HSA(FAF) (0.145 g, Sigma) was dissolved in 0.5 ml of water in a test tube. This solution was dispersed in the PMMA solution and cross-linked with glutaraldehyde for 16 hrs as described in Example 1. MS were washed to remove all PMMA dispersant by centrifugation with acetone (8X) then water (4X). After the last water wash the HSA(FAF)MS pellet was re-suspended in 10.0 ml of water. Aliquots (0.5 ml) were removed from the well-shaken sample and pipeted into three pre-weighed 13×100 mm test tubes, then placed in a 100° C. oven (National) to remove all water. Test tubes were cooled to r.t. and weighed, average of the three weights being used to determine the weight of MS per ml of water in the 10.0 ml volume. This yield was 0.114 g, 79% of HSA(FAF)MS. The average diameter of the MS was 32 $\mu$m as determined by optical microscopy.

EXAMPLE 6

Bovine, Dog and Rabbit Serum Albumin/Microspheres-Unquenched

Bovine serum albumin (BSA) (0.150 g), dog serum albumin (DSA) (0.150 g) and rabbit serum albumin (RSA) (0.150 g) obtained from Sigma (fraction V) were dissolved in 0.5 ml of water in test tube. The albumin/MS were then synthesized as described in Example 1 with a cross-linking reaction time of 16 hrs. The MS were washed with acetone, (8X, 10.0 ml volumes) to remove all PMMA, then with water (4X, 5.0 ml volumes). After the last water wash the brown pellets were re-suspended in 10.0 ml of water, and weight of albumin/MS per ml was determined as described above. The yield was 0.109 g, 73% (2) 0.103 g, 69% and (3) 0.128 g, 82%. Average diameter of MS were 28, 14 and 13 $\mu$m, respectively, as determined by optical microscopy. The MS are readily formed and are similar to MS produced from human albumin. This demonstrates the versatility of the procedure and the ability to synthesize MS from other mammelian protein which would be beneficial for veternary applications when MS containing therapeutic agents are required.

EXAMPLE 7

Polylysine (PLY)/Microspheres-Unquenched

PLY (0.151 g, MS 11,000, 0.11 $\mu$moles, Sigma) was dissolved in 0.5 ml of water in a test tube. This solution was dispersed in the PMMA mixture and PLY/MS were synthesized as described in Example 1 with a cross-linking reaction time of 2 hrs. The PLY/MS were washed with acetone to remove all PMMA, then with water. After the last water wash the yellow pellet was re-suspended in 10.0 ml of water and weight of the PLY/MS were determined as described above. This produced 0.120 g of PLY/MS in solution, 79% yield.

Polylysine (PLY) is a cationic polypeptide that consists of repeating units of amino residues with a net positive charge. PLY may be incorporated into the HSA matrix at various wt. concentrations. It is also possible to make PLY/MS. Glutaraldehyde was able to cross-link the PLY molecules in the same manner as albumin. PLY/MS would be advantageous because of its ability to conjugate acidic drugs by the formation of a salt complex.

EXAMPLE 8

Preparation of diisocyanate cross-linked bovine serum albumin(BSA) microspheres(MS)

BSA (0.161 g) was dissolved in 0.5 ml of water in a test tube. This solution was dispersed in the PMMA solution as described in Example 1. Tolylene 2,4-diisocyanate (TDI) (Aldrich) was used to cross-link the albumin. Aqueous TDC (80% 4.6 mmoles) 1.0 ml, and 1.0 ml of toluene were combined in a 2.0 ml volumetric flask. After mixing well, 1.0 ml of the TDI/toluene solution was added to the albumin dispersion. The dispersion was then mixed with a rotary mixer at r.t. for 21 hrs. BSA/MS were washed to remove all PMMA dispersant by centrifugation with acetone then water. After the water wash, the white pellet was frozen in liquid nitrogen and lyophilized yeilding 0.246 g of MS as a dry, free flowing white powder.

EXAMPLE 9

BSA (0.163 g) was dissolved in 0.5 ml of water in a test tube. The solution was dispersed in the PMMA solution as described in Example 1. Aqueous 1,6-diisocyanatohexane (DCH) (98% Aldrich), 1.0 ml (5.8 mmoles) and 1.0 ml toluene were combined in a 2.0 ml volumetric flask. After mixing well, 1.0 ml of the resulting solution was added to the albumin dispersion and mixed at r.t. for 21 hrs. The BSA/MS were washed and dehydrated according to the procedure in Example 8. The MS product was a white powder, 0.023 g, 76% yield.

EXAMPLE 10

Synthesis of Sub-Micron Microspheres

HSA, 0.164 g, was dissolved in 0.5 ml of water and added dropwise to 3.0 percent CAB in 25 ml of ethylene dichloride in 25×150 mm screw cap culture tubes. The mixture was dispersed with a Brinkman Homogenizer (PT 10–35) connected to a PT 20/TS probe generation at a setting of 6.5 for 10 mins. The dispersion was added dropwise to a 500 ml round bottom flask containing 100 ml of 3.0 percent CAB polymer solution and mixed at medium speed with a magnetic stirrer. A 4.0 ml glutaraldehyde saturated toluene solution was used for cross-linking (see Example 1) and the dispersion was allowed to react for 2 hrs at room temperature. The cross-linked MS were washed out with acetone and dehydrated as described in Example 1. This yielded 0.094 g of dry MS powder. Average size of the MS, determined using the scanning electron microscope, was 0.9 μm. The size distribution is shown in Table 1.

TABLE 1

| Sub-Micron: HSA/MS Size Distributions in CAB Dispersant: Energy 6.5 Time (10 mins) | |
|---|---|
| Size/μm | % Fraction |
| 0–0.5 | 6 |
| 0.5–0.75 | 49 |
| 0.75–1.0 | 13 |
| 1.0–1.25 | 19 |
| 1.25–1.5 | 10 |
| 1.5–1.75 | 3 |
| 1.75–2.0 | 0 |
| 2.0–4.5 | 0 |

EXAMPLE 11

Microspheres with Variations In Cross-Link Density and Hydration

BSA samples (1) 0.150 g, (2) 0.151 g (3) 0.150 g, and (4) 0.149 g were dissolved in 0.5 ml of water in test tubes. These solutions were dispersed in the PMMA mixture as described in Example 1. Glutaraldehyde was used for cross-linking and was diluted with water in the following ratios 1:1, 1:5, 1:10 and 1:20; this gave a final molar concentration of (a) 1.25 mmoles, (b) 0.5 mmoles, (c) 0.25 mmoles, and (d) 0.125 mmoles. The glutaraldehyde solutions were combined with toluene and dispersed as described in Example 1. After addition of the glutaraldehyde saturated toluene solutions (a) through (d) to the BSA/PMMA dispersions 1 through 4, they were mixed with a rotary mixer at r.t. for 22 hrs. After the final acetone wash and dehydration, the BSA/MS samples had a dry weight of (1) 0.125 g, (2) 0.140 g, (3) 0.135 g, and (4) 0.063 g. An aliquot of water (10.0 ml) was added to each sample and allowed to hydrate for 1.0 hr at room temperature. The dispersions were then centrifuged and all of the supernate was carefully removed with a pasteur pipet. BSA/MS were then reweighed to determine water content and were as follows: (1) 0.579 g, (2) 0.881 g, (3) 1.55 g, and (4) 0.969 g, by dividing the net weight by the dry weight the water content per mg of BSA/MS was determined. Average diameter of the MS for both the dry state and wet state was determined by optical microscopy. See Table 2.

TABLE 2

| Varying Cross-Link Density and Hydration of BSA/MS (Glutaraldehyde Cross-Linking) | | | | |
|---|---|---|---|---|
| Glutaraldehyde Concentration (mmoles) | Mean Diameter Dehydrated (μm) | Mean Diameter Hydrated (μm) | mg Water Uptake/ mg of BSA/HSA | % Hydration |
| 1.25 | 14 | 17 | 4.6 | 82 |
| 0.50 | 13 | 21 | 6.3 | 86 |
| 0.25 | 10 | 23 | 11.5 | 92 |
| 0.13 | 17 | 37 | 15.4 | 94 |

EXAMPLE 12

BSA samples (1) 0.151 g, (2) 1.157 g, (3) 0.148 g and (4) 0.150 g were dissolved in 0.5 ml of water in test tubes. These solutions were then dispersed in the PMMA mixture as described in Example 1. Dilutions of tolylene 2,4-dissocyanate (TDC) were used for cross-linking and were prepared as follows. In four 10.0 ml volumetric flasks: (a) 0.4 ml, (b) 0.2 ml, (3) 0.1 ml, and (d) 0.07 ml of TDC were diluted with toluene. This gave final molar concentrations of (a) 0.18 mmoles (b) 0.092 mmoles (c) 0.046 mmoles and (d) 0.031 mmoles. One ml of the TDC/toluene solutions (a) through (d) were added to the albumin dispersions 1 through 4. The dispersions were then mixed with a rotary mixer at r.t. for 22 hrs. After the final acetone wash and dehydration, the BSA/MS samples had a dry weight of (1) 0.176 g (2) 0.171 g (3) 0.149 g and (4) 0.150 g. After hydration and removal of excess water as described in Example 11, the BSA/MS samples were re-weighed; this yielded (1) 0.314 g (2) 0.643 g (3) 1.950 g and (4) 3.664 g. The water content of the MS were then calculated for each sample as described in Example 11. Average diameter of the BSA/MS for both the dry state and wet state were determined by optical microscopy. See Table 3.

TABLE 3

| Varying Cross-Link Density and Hydration of BSA/MS (TDI Cross-Linking) | | | | |
|---|---|---|---|---|
| Concentration of TDI (mmoles) | Mean Diameter Dehydrated (μm) | Mean Diameter Hydrated (μm) | mg Water Uptake/ mg of BSA/MS | % Hydration |
| 0.18 | 18 | 19 | 1.8 | 64 |
| 0.092 | 18 | 22 | 3.6 | 78 |
| 0.046 | 21 | 30 | 13 | 93 |
| 0.031 | 16 | 40 | 24 | 96 |

EXAMPLE 13

BSA samples (1) 0.150 g (2) 0.166 g (3) 0.151 g (4) 0.149 g and (5) 0.160 g were dissolved in 0.5 ml of water in test tubes. These solutions were then dispersed in the PMMA mixture as described in Example 1. Dilutions of 1,6-diisocyanatohexane (DCH) were used for cross-linking and were prepared as follows: In five 10.0 ml volumetric flasks: (a) 5.0 ml (b) 2.0 ml (c) 1.0 ml (d) 0.4 ml and (e) 0.2 ml of DCH were added and diluted with toluene. This gave final molar concentrations of (a) 2.9 mmoles (b) 1.16 mmoles (c) 0.58 mmoles (d) 0.23 mmoles and (e) 0.12 mmoles. One ml of the DCH/toluene solutions (a) through (e) were added to the albumin dispersions (1) through (5). The dispersions were then mixed with a rotary mixer at r.t. for 22 hrs. After the final acetone wash and dehydration, the BSA/MS samples had a dry weight of (1) 0.140 g (2) 0.150 g (3) 0.141 g (4) 0.129 g and (5) 0.144 g. After hydration and removal of excess water as described in Example 11, the BSA/MS samples were re-weighed; this yielded (1) 0.240 g (2) 0.593 g (3) 0.898 g (4) 2.006 g and (5) 2.854 g. The water content of the BSA/MS were then determined for each sample as described in Example 11. Average diameter of the BSA/MS samples for both the dry state and wet state were determined by optical microscopy. See Table 4.

TABLE 4

Varying Cross-Link Density and Hydration of BSA/MS (DCH Cross-Linking)

| Concentration of DCH (mmoles) | Mean Diameter Dehydrated ($\mu$m) | Mean Diameter Hydrated ($\mu$m) | mg Water Uptake/ mg BSA/MS | % Hydration |
|---|---|---|---|---|
| 2.9 | 18 | 20 | 1.7 | 63 |
| 1.16 | 21 | 29 | 3.7 | 79 |
| 0.58 | 13 | 28 | 6.4 | 86 |
| 0.23 | 17 | 38 | 16.0 | 94 |
| 0.12 | 16 | 50 | 20.0 | 95 |

The free functional groups on the cross-linked microspheres are capable of reaction with a wide variety of substances containing functional groups reactive with those on the microspheres whereby the substance is covalently or otherwise boned to the microspheres. There is virtually no limit to the types of substances which can be bound to the microspheres in this manner. Thus, the microspheres may be reacted with aminoalcohols, e.g., 2-aminoethanol or amino acids, e.g., glycine, to enhance hydrophilicity; coupled with, e.g., amino group containing drugs (adriamycin) for administration to a biological system or covalently bonded to large protein molecules such as lectins, enzymes or antibodies. In addition, changes in surface functionability of the microspheres may be used to enhance tissue immobilization by covalent or physical binding for specific tissue targeting using biospecific affinity ligands, e.g., tumor-specific immune assay reagents.

Whereas protein and polypeptide microspheres containing entrapped or encapsulated substances prepared according to prior art methods are relatively hydrophobic requiring surfactants for dispersion in aqueous media and make post-forming aqueous chemical modification difficult, those of the present invention are hydrophilic, capable of dispersion in aqueous media in relatively large amounts without the necessity for surfactants and are readily useful for post-forming absorption of biologically active agents or chemical modification in aqueous media.

Where it is desired to couple the microspheres with a substance which does not contain a functional group reactible with any free functional group in the cross-linked microsphere, the latter may first be reacted with a linking or bridging agent which has at least one functional group capable of reacting with the free functional group in the microspheres and at least one additional functional group which will react with the desired surfactant to covalently bond it to the microsphere.

Suitable substances for chemical or physical bonding to the microspheres, depending, of course, upon the nature of the free functional groups thereon or the ability of the drug to naturally bind thereto include antitumor agents, e.g., adriamycin, bleomycin, chlorambucil, mitomycin C, etc., antibiotics, e.g., streptomycin, gentamycin, tobramycin, formycin A, etc., steroids, e.g., hydrocortisone phosphate, progesterone and other contraceptive hormones, etc.

The term "biological system" as employed herein, is intended to include any living system, e.g., lower animal, human, plant, etc., to which a biologically active substance may be administered for therapeutic, diagnostic or other biological purpose.

The following non-limiting examples illustrate the embodiment of the invention wherein the microspheres are bonded physically or chemically (covalently) to substances. Physical binding or association of drugs occurs readily with albumin and is satisfactory for many types of albumin-drug microsphere systems, especially where rapid drug release is desired. Chemical binding occurs via available reactive functional groups. In the following examples, the term "quench" refers to the reaction of free functional groups in the interior and/or on the surface of the microspheres with a substance containing a functional group reactive therewith.

EXAMPLE 14

Measurement of Free Reactive Aldehyde Groups in Microspheres

Tritiated Leucine

HSA/MS (10 $\mu$m average diameter) were prepared as described in Example 1. The cross-linked HSA/MS were divided into two samples. One was quenched as described hereinbelow with 0.5 ml of 2-aminoethanol while the other sample was left unquenched. Tritiated leucine (New England Nuclear) specific activity 134.2 $\mu$Ci/mmoles/ml, was diluted with a L-leucine carrier to a final activity of 5 $\mu$curie/50 mmoles/ml. One ml of the isotope solution was added to each of three samples of 7.4 mg/ml unquenched and three samples of 8.0 mg/ml quenched MS in test tubes. The samples were incubated for 40 mins in a table top sonicator (E/MC RA Research), then washed four times with water by centrifugation (1000 RPM$\times$2 mins). MS pellets were re-suspended in 2.0 ml of a scintillation cocktail (Aquasol New England Nuclear). From each of the solutions 1.0, 0.5, and 0.25 ml aliquots were removed and added to scintillation counter containers. The final volumes were adjusted to 15.0 ml with additional cocktail solution. Activity was determined using a Beckman Model 230 scintillation counter and values plotted against prepared standards. See Table 5.

TABLE 5

Concentration of Reactive Aldehyde Groups for HSA/MS by Binding of Tritium Labeled Leucine

| Physical or Chemical Binding of Leucine | Leucine (moles) Bound/ml of MS | # of Leucine 10 $\mu$m MS | # Reactive CHO/MS* |
|---|---|---|---|
| HSA/MS-Quenched | $8.8 \times 10^{-2}$ | $5.5 \times 10^7$ | — |
| HSA/MS-Unquenched | $1.3 \times 10^{-1}$ | $7.8 \times 10^7$ | — |
| Chemically Reacted (MS-U—MS-Q) | $4.0 \times 10^{-2}$ | $2.4 \times 10^7$ | $2.4 \times 10^7$ |

*Assume one bound leucine equals one reactive aldehyde group

EXAMPLE 15

Tritiated Concanavalin A (Con-A) Binding As a Function of Particle Size

HSA/MS samples were prepared as described in Example 1. This produced MS with an average diameter of 30 μm, 12 μm, and 5 μm. The cross-linked MS were divided into two samples, quenched and unquenched. Tritiated Con-A (New England Nuclear Corp.) specific activity 42.4 μCl/mmole/ml, was diluted with a carrier (Con-A, Sigma) to a final activity of 1.0 μCi/0.136 μmoles/ml, in 0.01 molar sodium phosphate buffer at pH 6.9. Two ml of the isotope solution was added to one sample of each particle size for both unquenched and quenched in test tubes. The samples were incubated for one hr in a table top sonicator, washed and re-suspended in a scintillation cocktail as described in Example 14. Activity was determined using a scintillation counter and values plotted against prepared standards. See Table 6.

TABLE 6

Con-A Binding to HSA/MS as a Function of MS Size

| Mean Diameter (μm) | Con-A (μmoles) Bound/mg of HSA/MS-U | Con-A (μmoles) Bound/mg of HSA/MS-Q | Reacted Con-A μmoles/mg (U-Q) |
| --- | --- | --- | --- |
| 30 | $2.6 \times 10^{-4}$ | $2.6 \times 10^{-4}$ | 0 |
| 12 | $3.7 \times 10^{-4}$ | $3.2 \times 10^{-4}$ | $0.5 \times 10^{-4}$ |
| 5 | $6.7 \times 10^{-4}$ | $4.0 \times 10^{-4}$ | $2.7 \times 10^{-4}$ |

EXAMPLE 17

Physical Analysis of Surface Properties of Microspheres, Capillary Wetting as a Function of Quenching HSA/MS (30 μm average diameter) were prepared as described in Example 1. The HSA/MS were divided into two samples. One was quenched with glycine, as described hereinbelow, and the other sample was left unquenched, HSA/MS were dehydrated with acetone and air dried. Pasteur pipets (10 cm×1 mm I.D.) were used as the capillary column. By gently pushing the pipet through a glass fiber (3 cm diameter, Gelman Type A-E) a plug was formed in the end of the column. HSA/MS samples were loaded into the column and packed by holding the capillary tube vertically on the rubber tip of the vortex genie, then vibrating the tube for 20 to 30 seconds at a speed setting of one. Columns were packed with HSA/MS to a height of 3.0 cm from top of glass fiber plug. The capillary tube was mounted vertically and placed in a plexiglass tank (10 cm×10 cm×5 cm filled with water) to a depth of one cm. The height of the water rise up the column was measured as a function of time. Both quenched and unquenched samples were run and the data taken (Table 7) was compared to HSA/MS produced by the prior art vegetable oil method (hydrophobic)

TABLE 7

Hydrophilic Measurements of HSA/MS as a Function of Surface Properties by Capillary Rise

| Time (mins) | HSA/MS Unquenched Height (mm) | HSA/MS Quenched Height (mm) | HSA/MS Hydrophobic Height (mm) |
| --- | --- | --- | --- |
| 15 | 2.4 | 9.4 | 0.1 |
| 35 | 2.7 | 13.7 | 0.1 |
| 45 | 2.9 | 17.2 | 0.1 |
| 60 | 3.2 | 20.1 | 0.1 |
| 75 | 3.4 | 22.5 | 0.1 |
| 90 | 3.5 | 24.9 | 0.1 |
| 105 | 3.7 | 26.8 | 0.1 |
| 120 | 3.8 | 28.6 | 0.1 |

EXAMPLE 18

Human Serum Albumin/Microspheres-Quenched (Q)

HSA/MS were synthesized and washed as described in Example 1. After the last acetone wash, the HSA/MS pellet was re-suspended with 5.0 ml of water, briefly agitated and centrifuged. This was repeated four additional times. After the last water wash, the HSA/MS pellet was re-suspended in 5.0 ml of 1.0 molar glycine HCl to "quench" the residual reactive aldehyde groups. The HSA/MS glycine solution was mixed at r.t. for 22 hrs with a rotary mixer. MS were removed from the unreacted glycine by centrifugation. After decanting the glycine supernate the HSA/MS pellet was re-suspended in a 50 ml polypropylene centrifuge tube (Corning) with 45.0 ml of water (pH 3.0), briefly agitated and centrifuged (2000 RPM×2 min). This wash procedure was repeated three times. The process was repeated again with water at pH 7.0. After the last water wash, MS were dehydrated with acetone (4x, 100% acteone in 10.0 ml volumes) and allowed to air dry. The product was a yellowish brown powder, 115 g, 77% yield. The average size of the MS was 26 μm in diameter as determined with optical microscopy.

The following non-limiting examples illustrate the embodiment of the invention wherein other non-cross-linking substance (macromolecules) are entrapped in the albumin microsphere producing a composite of the albumin with the substance.

EXAMPLE 19

Human Serum Albumin/Microspheres Containing Polyglutamic Acid (PGA)-Unquenched PGA (60,000 MW, Sigma) was added into HSA/MS in concentrations of 12, 16 and 22 wt %. The PGA-HSA/MS were synthesized, washed and dehydrated as described in Example 1. Samples were prepared with the following weight ratios of HSA and PGA;

| | HSA | PGA |
| --- | --- | --- |
| 1. | 0.134 g | 0.017 g (0.3 μmoles) |
| 2. | 0.129 g | 0.025 g (0.4 μmoles) |
| 3. | 0.119 g | 0.032 g (0.5 μmoles) |

The yields of the resulting cross-linked HSA/PGA/MS were as follows: (1) 0.117 g, 78% (2) 0.134 g, 87% and (3) 0.124 g, 82%. The average diameter of the microspheres were 34, 29, and 29 μm, respectively, as determined by optical microscopy.

EXAMPLE 20

Human Serum Albumin/Microspheres Containing Polyglutamic Acid-Quenched

HSA/PGA/MS were synthesized as described in Example 19. The amount of added PGA was 11, 15 and 19 wt %. The HSA/PGA/MS were then quenched with glycine to "cap" residual aldehyde groups. Samples were prepared with the following weight ratios of HSA and PGA;

|    | HSA     | PGA                    |
|----|---------|------------------------|
| 1. | 0.133 g | 0.016 g (0.30 μmoles)  |
| 2. | 0.127 g | 0.022 g (0.38 μmoles)  |
| 3. | 0.121 g | 0.029 g (0.48 μmoles)  |

The yields were as follows: (1) 0.115 g, 77% (2) 0.128 g, 85% and (3) 0.117 g, 78%. The average diameter of the microspheres were 23, 28, and 28 μm, respectively, as determined by optical microscopy.

Modification of Albumin Microspheres Cross-Linked with Tolylene 2,4-Diisocyanate (TDI)

EXAMPLE 21

Bovine Serum Albumin with 14% Polyglutamic Acid-Unquenched

BSA (0.131 g) and PGA (0.022 g) were combined and dissolved in 0.5 ml of water in a test tube. The albumin solution was dispersed in the PMMA mixture as described in Example 1. A 0.046 mmolar solution of TDI was prepared from 80% aqueous TDI and toluene. After mixing well, 1.0 ml of the solution was added to the albumin dispersion and mixed at r.t. for 12 hrs with a rotary mixer. BSA/MA were washed to remove all of the PMMA dispersant with acetone and dehydrated as described in Example 1. The product was a white powder, 0.146 g, 95% yield.

EXAMPLE 22

Bovine Serum Albumin with 14% Polyglutamic Acid Microspheres-Quenched

BSA (0.132 g) and PGA (0.021 g) were combined and dissolved in 0.5 ml of water in a test tube. The albumin solution was dispersed in the PMMA mixture, synthesized, washed and quenched as described in Example 18. The product was a white powder, 0.067 g, 44% yield.

EXAMPLE 23

Bovine Serum Albumin Microspheres Containing 11.7% Carboxymethyldextran (CMD)-Unquenched CMD was synthesized using the procedure of Pitha et al, J. Natl. Cancer Inst., Vol. 65, p. 5 (1980). Dextran (40,000 MW, Sigma) (5.0 g) was dissolved in 5.0 ml of water. This solution was added to 38 ml of 40% sodium hydroxide and 27 g of chloroacetic acid in a 125 ml erlenmeyer flask. The suspension was stirred for 12.0 hrs at room temperature. After this process was repeated twice, the solution was extensively dialyzed against water using membrane tubing (Spectropor) with a 6,000–8,000 MW cutoff, inside diameter of the tubing was 25.5 mm. The modified dextran was frozen in liquid nitrogen and lyophilized. Yield of product was not recorded. The carboxylic content was 4.4 μmoles of carboxyl groups per mg of material.

BSA (0.135 g) and CMD (0.018 g) were combined and dissolved with 0.5 ml of water in a test tube. The protein/dextran solution was dispersed in the PMMA mixture and the CMD-BSA/MS were synthesized as described above. The product was a white powder, 0.092 g, 60% yield.

EXAMPLE 24

Bovine Serum Albumin Microspheres Containing 15% Carboxymethyldextran-Quenched

BSA (0.139 g) and CMD (0.024 g) were combined and dissolved in 0.5 ml of water in a test tube. The protein/dextran solution was dispersed in the PMMA mixture and the CMD-BSA/MS were synthesized as described in Example 23. The CMD-BSA/MS were washed to remove all of the PMMA dispersant, quenched and dehydrated as described in Example 18. The product was white powder, 0.049 g, 30% yield.

The incorporation of PGA into HSA/MS increased anionicity. For applications (e.g. experimental treatment of Brucellosis in cattle) involving large scale production of anionic/MS, the use of PGA might be limited because of its high cost. A viable alternative to PGA is carboxymethyldextran (CMD). The modified dextran is inexpensive and has the physical properties (high content of functional carboxyl groups) required to increase anionicity of the albumin/MS.

EXAMPLE 25

18 wt % Adriamycin-Human Serum Albumin/Microspheres-Unquenched

Adriamycin in HCL (AD) (52.3 mg) (Farmitalia Carlo ERBA) was dissolved in 25.0 ml of water, 5.0 ml of the clear dark red solution (10.46 mg AD) was combined with 9.99 mg of the HSA/MS-U (synthesized in Example 1) in a screw cap test tube. The pH of the cloudy red mixture was adjusted from 4.00 to 5.70 by the addition of 0.1N NaOH and mixed with a rotary mixer at 4° C. in the dark for 11 hrs. The mixture was centrifuged (2000 RPM×2 mins) and the light red supernate was carefully removed with a pasteur pipet and saved for analysis. The dark red pellet was re-suspended in 10.0 ml of water, briefly stirred, centrifuged and the supernate saved for analysis. This was repeated five times. After the last wash, the AD-HSA/MS-U were dehydrated with acetone and allowed to air dry. The MS product was a dark red powder 11.6 mg, 97% yield, containing 18 wt % AD.

In Vitro AD Release: Dynamic Column Elution Method

A dynamic flow column was used to measure in vitro drug release; 2.0 ml of water was added to the dry AD-HSA/MS-U (11.61 mg), the resulting red slurry was pipeted into a 140 mm×7 mm glass column. The ends of the column were modified with chromatography caps packed with glass wool and attached to threaded zero-volume collectors that were connected to 1.0 mm I.D. teflon tubing. Care was taken to ensure that all the AD-HSA/MS-U were transferred into the column. The column was then placed in a circulating water bath at 37° C. Physiological saline was pumped through the column at 0.4 ml/min with an HPLC pump (ALTEX model 110A). Fractions were collected every 30 mins for 15 hrs at 4° C. Wash in each fraction was analyzed at 480 nm by UV/VIS to determine the AD concentration eluted from the AD/HSA/MS-U. All subsequent dynamic flow in vitro release studies were performed as just described unless otherwise noted. See Table 8.

TABLE 8

AD Release From 18 wt % AD—HSA/MS—U (29 μm)
11.61 mg AD—HSA/MS—U (2.09 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.40 | 0.09 | 0.03 | 0.01 | 0.01 | 0.0 | 0.0 |
| Cumulative Wt AD (mg) | 0.40 | 0.49 | 0.52 | 0.53 | 0.54 | 0.54 | 0.54 |
| % Released | 19 | 24 | 25 | 25 | 26 | 26 | 26 |

EXAMPLE 26

33 wt % Adriamycin-Polyglutamic Acid (12%)-Human-Serum Albumin/Microspheres-Unquenched A volume of 5.0 ml of the stock AD solution (10.46 mg AD) prepared in Example 28 was combined with 11.39 mg of PGA (12%)-HSA/MS-U (synthesized in Example 19) in a screw cap test tube. The pH of the cloudy red mixture was adjusted from 4.45 to 5.84 by the addition of 0.1N NaOH and mixed with a rotary mixer at 4° C. in the dark for 11 hrs. The AD-PGA (12%)-HSA/MS-U were removed from the drug free solution and the bound concentration of AD was determined as described above. The product was a dark red powder, 15.6 mg, 91% yield. Concentration of the bound AD to PGA (12%)-HSA/MS-U was 5.57 mg or 33 wt %.

In Vitro Release

The in vitro release of the free AD from AD-PGA (2%)/MS-U (15.6 mg) was measured and the results set forth in Table 9.

TABLE 9

AD Release from 33 wt % AD-PGA(11%)-HSA/MS-U (34 μm)
15.62 mg AD-PGA(11%)-HSA/MS-U (5.15 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 1.11 | 0.41 | 0.16 | 0.08 | 0.08 | 0.07 | 0.05 |
| Cumulative Wt AD (mg) | 1.11 | 1.52 | 1.68 | 1.76 | 1.84 | 1.91 | 1.96 |
| % Released | 22 | 30 | 33 | 34 | 36 | 37 | 38 |

EXAMPLE 27

39 wt % Adriamycin-Polyglutamic Acid (16%)-Human-Serum Albumin/Microspheres-Unquenched A volume of 5.0 ml of the stock AD solution (10.46 mg AD) prepared in Example 25 was combined with 10.40 mg of PGA (16%)-HSA/MS-U (synthesized in Example 19) in a screw cap test tube. The pH of the cloudy red mixture was adjusted from 4.32 to 5.80 by the addition of 0.1N NaOH and mixed with a rotary mixer in the dark at 4° C. for 11 hrs. AD-PGA (16%)-HSA/MS-U were washed out of the free drug solution, and concentration of the bound AD was determined as described above. The product was a dark red powder, 11.1 mg, 65% yield. Concentration of the bound AD was 6.70 mg or 39 wt %.

In vitro Release

The in vitro release results of free AD from AD-PGA (16%)-HSA/MS-U (11.1 mg) are set forth in Table 10.

TABLE 10

AD Release From 39 wt % AD-PGA(16%)-HSA/MS-U (29 μm)
11.08 mg AD-PGA(16%)-HSA/MS-U (4.33 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.85 | 0.29 | 0.19 | 0.14 | 0.12 | 0.11 | 0.09 |
| Cumulative Wt AD (mg) | 0.85 | 1.14 | 1.33 | 1.47 | 1.59 | 1.70 | 1.79 |
| % Released | 20 | 26 | 31 | 34 | 37 | 39 | 41 |

EXAMPLE 28

46 wt % Adriamycin-Polyglutamic Acid (22%)-Human Serum Albumin/Microspheres-Unquenched A volume consisting of 5.0 ml of the stock AD solution (10.46 mg AD) prepared in Example 25 was combined with 10.1 mg of PGA(22%)-HSA/MS-U (synthesized in Example 19) in a screw cap test tube. The pH of the cloudy red mixture was adjusted from 4.43 to 5.80 by the addition of 0.1N NaOH and mixed with a rotary mixer in the dark at 4° C. for 11 hrs. AD-PGA(22%)-HSA/MS-U were washed out of the free drug solution, dehydrated and concentration of the bound AD was determined as described above. The product was a dark red powder 14.7 mg, 78% yield. Concentration of the bound AD was 8.61 mg or 46 wt %.

In Vitro Release

The release of the free AD from the AD-PGA(22%)-HSA/MS-U (14.7 mg) produced in this procedure was measured and the results set forth in Table 11.

TABLE 11

AD Release from 46 wt % AD-PGA(22%)-HSA/MS-U (29 μm)
8.41 mg AD-PGA(22%)-HSA/MS-U (3.86 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 1.01 | 0.24 | 0.26 | 0.14 | 0.11 | 0.08 | 0.07 |
| Cumulative Wt AD (mg) | 1.01 | 1.25 | 1.51 | 1.65 | 1.76 | 1.84 | 1.91 |
| % Released | 26 | 32 | 39 | 43 | 46 | 48 | 50 |

EXAMPLE 29

18 wt % Adriamycin-Human Serum Albumin/Microspheres-Quenched

AD (50.5 mg), was dissolved in 25.0 ml of water in a volumetric flask. A volume consisting of 5.0 ml of the clear dark red solution (10.1 mg AD) was combined with 10.7 mg of HSA/MS-Q (Example 18) in a screw cap test tube. The pH of the cloudy red mixture was adjusted from 2.99 to 5.83 by the addition of 0.1N NaOH and mixed with a rotary mixer at 4° C. in the dark for 11 hrs. AD-HSA/MS-Q were removed from the free AD solution, washed, and dehydrated as described in Example 28. The wash was saved for analysis. The product was dark red powder, 7.1 mg, 54% yield.

In Vitro Release

The release of free AD from the AD-HSA/MS-Q (7.1 mg) produced in this procedure was measured and the results set forth in Table 12.

TABLE 12

AD Release from 18 wt % AD-HSA/MS-Q (26 μm)
7.08 mg AD-HSA/MS-Q (1.28 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.68 | 0.21 | 0.12 | 0.06 | 0.03 | 0.03 | 0.01 |
| Cumulative Wt AD (mg) | 0.68 | 0.89 | 1.01 | 1.07 | 1.10 | 1.13 | 1.14 |
| % Released | 53 | 70 | 77 | 82 | 85 | 87 | 88 |

EXAMPLE 30

21 wt % Adriamycin-Polyglutamic Acid (11%)-Human Serum Albumin/Microspheres-Quenched A volume consisting of 5.0 ml of the stock AD solution (10.1 mg AD) prepared as above was combined with 11.0 mg of PGA (11%)-HSA/MS-Q (synthesized in Example 20) in a screw cap test tube. The pH of the cloudy red mixture was adjusted from 3.46 to 5.81 by the addition of 0.1N NaOH and mixed with a rotary mixer at 4° C. in the dark for 11 hrs. AD-PGA (11%)-HSA/MS-Q were washed out of the free AD solution, dehydrated and concentration of the bound drug was determined as above. The product was a dark red powder, 10.88 mg, 82% yield. Concentration of the bound AD was 2.83 mg or 21 wt %.

In vitro Release

The release of the free AD from the AD-PGA(11%)-HSA/MS-Q (10.9 mg) was measured and the results set forth in Table 13.

TABLE 13

AD Release from 21 wt % AD-PGA (11%)-HSA/MS-Q (23 μm)
10.88 mg AD-PGA (11%)-HSA/MS-Q (2.23 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 1.30 | 0.21 | 0.10 | 0.04 | 0.01 | 0.02 | 0.01 |
| Cumulative Wt AD (mg) | 1.29 | 1.50 | 1.60 | 1.64 | 1.65 | 1.67 | 1.68 |
| % Released | 58 | 67 | 72 | 73 | 74 | 75 | 75 |

EXAMPLE 31

25 wt % Adriamycin-Polyglutamic Acid (15%)-Human Serum Albumin/Microspheres-Quenched A volume consisting of 5.0 ml of the stock AD solution (10.1 mg AD) prepared as above was combined with 9.9 mg of PGA (15%)-HSA/MS-Q (synthesized in Example 20) in a screw cap test tube. The pH of the cloudy red mixture was adjusted from 3.59 to 5.84 by the addition of 0.1N NaOH and mixed with a rotary mixer at 4° C. in the dark for 11 hrs. AD-PGA(15%)-HSA/MS-Q were washed out of the free AD solution, dehydrated and concentration of the bound drug was determined as described above. The product was dark red powder, 5.7 mg, 43% yield. Concentration of the bound AD was 3.33 mg or 25 wt %.

In vitro Release

The release of the free AD from the AD-PGA(15%)-HSA/MS-Q (5.7 mg) was measured and the results set forth in Table 14.

TABLE 14

AD Release from 25 wt % AD-PGA (15%)-HSA/MS-Q (28 μm)
5.70 mg AD-PGA (15%)-HSA/MS-Q (1.43 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.77 | 0.08 | 0.02 | 0.02 | 0.02 | 0.02 | 0.01 |
| Cumulative Wt AD (mg) | 0.77 | 0.85 | 0.87 | 0.89 | 0.91 | 0.93 | 0.94 |
| % Released | 54 | 59 | 61 | 62 | 64 | 65 | 66 |

EXAMPLE 32

33 wt % Adriamycin-Polyglutamic Acid (19%)-Human Serum Albumin/Microspheres-Quenched A volume consisting of 5.0 ml of the stock adriamycin solution (10.1 mg AD) prepared as above was combined with 10.1 mg of PGA (19%)-HSA/MS-Q (synthesized in Example 20) in a screw cap test tube. The pH of the cloudy red mixture was adjusted from 3.71 to 5.84 by the addition of 0.1N NaOH and mixed with a rotary mixer at 4° C. in the dark for 11 hrs. AD-PGA (19%)-HSA/MS-Q were washed out of the free AD solution, dehydrated and concentration of the bound drug was determined as described above. The product was a dark red powder, 7.9 mg, 53% yield. Concentration of the bound drug was 4.9 mg or 33 wt %.

In vitro Release

The release of the free AD from the AD-PGA (19%)-HSA/MS-Q (7.9 mg) was measured and the results set forth in Table 15.

TABLE 15

AD Release from 33 wt % AD-PGA (19%)-HSA/MS-Q (24 μm)
7.88 mg AD-PGA (19%)-HSA/MS-Q (2.58 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.77 | 0.20 | 0.14 | 0.09 | 0.08 | 0.07 | 0.07 |
| Cumulative Wt AD (mg) | 0.77 | 0.97 | 1.11 | 1.20 | 1.28 | 1.35 | 1.42 |
| % Total AD | 30 | 38 | 43 | 47 | 50 | 52 | 55 |

EXAMPLE 33

Ion Exchange Release Properties of Adriamycin-Albumin/Microspheres-Quenched

AD was bound to (1) HSA/MS-Q (quenched with 2-aminoethanol), (2) HSA-MS-Q (quenched with glycine) and (3) PGA (15%)-HSA/MS-Q according to the procedure described above. MS were washed out of the free drug solution, dehydrated and concentration of the bound AD was determined as described above. After dehydration, the AD-MS had a yield of (1) 8.28 mg, 75%, (2) 7.98 mg, 77% and (3) 9.50 mg, 57%. Concentration of the bound drug for each sample was (1) 1.4 mg or 14%, (2) 1.6 mg or 20% and (3) 4.8 mg or 28%.

In vitro Release

The AD-albumin/MS samples were separately loaded in the release column as described above. Water was used as the mobile phase for the first 5.0 hrs, then exchanged for physiological saline for the remainder of the experiment. Release data is set forth in Tables 16, 17 and 18.

TABLE 16

AD Release from 14 wt %
AD-HSA/MS-Q (aminoethanol) (25 μm)
8.28 mg AD-HSA/MS-Q (1.16 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.16 | 0.12 | 0.17 | 0.30 | 0.05 | 0.02 | 0.0 |
| Cumulative Wt AD (mg) | 0.16 | 0.28 | 0.45 | 0.75 | 0.80 | 0.82 | 0.82 |
| % Released | 14 | 24 | 39 | 65 | 69 | 71 | 71 |

TABLE 17

AD Release from 20 wt % AD-HSA/MS-Q (glycine) (25 μm)
7.98 mg AD-HSA/MS-Q (1.60 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.14 | 0.12 | 0.38 | 0.18 | 0.08 | 0.08 | 0.08 |
| Cumulative Wt AD (mg) | 0.14 | 0.26 | 0.64 | 0.82 | 0.90 | 0.98 | 1.06 |
| % Released | 9 | 16 | 40 | 52 | 56 | 61 | 66 |

TABLE 18

AD Release from 28 wt % AD-PGA (15%)-HSA/MS-Q (28 μm)
9.54 mg AD-PGA (15%)-HSA/MS-Q (2.67 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.08 | 0.03 | 0.23 | 0.79 | 0.25 | 0.13 | 0.12 |
| Cumulative Wt AD (mg) | 0.08 | 0.11 | 0.34 | 0.13 | 1.38 | 1.51 | 1.63 |
| % Released | 3 | 4 | 13 | 42 | 52 | 57 | 61 |

EXAMPLE 34

In vitro Release of Adriamycin from Albumin/Microspheres in a Static System

PGA(10%)-HSA/MS-Q containing AD, synthesized as described above were washed out of the free AD solution, dehydrated and concentration of the bound AD was determined as described above. The product was a dark red powder, 6.1 mg, 75% yield. The concentration of the bound drug was 2.6 mg or 31.7 wt %.

In vitro Release

The AD-PGA(10%)-HSA/MS (6.1 mg) were combined with 2.0 ml of physiological saline in a screw cap test tube and placed in a 37° C. shaker water bath. Every 30 mins, the cloudy red mixture was centrifuged and 50 μl was removed from the clear red supernate, diluted in 5.0 ml of physiological saline. The concentration of the released AD was then determined as previously described above. This procedure was repeated until the amount of release drug remained constant (i.e., no more AD released). The AD-PGA(10%)-HSA/MS-Q were then washed (5X) with 10.0 ml volumes of water to remove all free AD. After the last water wash was decanted, the MS were re-suspended with 2.0 ml of saline and the process duplicated for the remainder of the experiment (15 hrs.)

EXAMPLE 35

In Vivo Studies

Toxicity of Adriamycin-Polyglutamic Acid (15%)-Human Serum Albumin/Microspheres-Quenched in CD-1 Mice AD-PGA(15%)-HSA/MS-Q were synthesized according to the procedure described above. The product was a dark red powder with 27 wt % bound AD and total yield of 76%. MS had a size range of 20–40 μm.

CD-1 white female mice, 5–7 weeks of age, weighing 30–33 g were injected by the intraperitoneal (i.p.) route with AD at concentrations of 0.6 mg and 1.5 mg dissolved in 0.5 ml of sterile saline. A second group of animals were injected with AD-PGA(15%)-HSA/MS-Q with 0.6, 1.5, and 2.5 mg of bound AD. For each concentration of the free and bound drug, 5 mice were used. PGA(15%)-HSA/MS-Q without AD was used for a control group and injected in equivalent weight amounts. Animals were then observed over a two-month period and fatalities were recorded for each group and tabulated. See Table 19.

TABLE 19

Toxicity of AD-PGA-HSA/MS-U in CD-1 Mice by i.p. Injection

| Preparation and dose | Survival from Time of Administration | | | | |
|---|---|---|---|---|---|
| | 7 days | 14 days | 21 days | 28 days | 35 days |
| AD (0.6 mg) | 5/5 | 1/5 | 1/5 | 1/5 | 1/5 |
| AD (1.5 mg) | 5/5 | 0/5 | — | — | — |
| AD-PGA-HSA/MS (AD 0.6 mg) (2.22 mg MS) | 5/5 | 5/5 | 5/5 | 5/5 | 5/5 |
| AD-PGA-HSA/MS AD 1.5 mg) (4.44 mg MS) | 5/5 | 5/5 | 5/5 | 5/5 | 5/2 |
| AD-PGA-HSA/MS (AD 2.5 mg) (9.26 mg MS) | 5/5 | 4/5 | 1/5 | 0/5 | — |
| PGA-HSA/MS (2.22 mg MS) | 5/5 | 5/5 | 5/5 | 5/5 | 5/5 |
| PGA-HSA/MS (4.44 mg MS) | 5/5 | 5/5 | 5/5 | 5/5 | 5/5 |
| PGA-HSA/MS (9.26 mg MS) | 5/5 | 5/5 | 5/5 | 5/5 | 5/5 |

EXAMPLE 36

HSA/MS were readily prepared as described above containing up to 18 wt % of the anti-tumor drug adriamycin (AD). The binding of AD to HSA/MS involved two mechanisms; (1) the covalent attachment of the primary amine associated with AD to free reactive mono-dialdehydes on HS/MS-unquenched (U) and (2) physical binding of AD to HSA/MS-quenched (Q).

Terry, R.N., M.S. Thesis, University of Florida (1980) demonstrated that PGA readily formed stoichiometric ionic salts with basic drugs such as AD. This is due to interactions between the anionic carboxyl groups associated with PGA and the cationic primary amine group located on the daunosamine ring of AD. Terry also found that by subjecting the PGA-AD complex to an appropriate electrolyte, the ionic salt would dissociate and release the AD. The addition of PGA to the HSA/MS made possible the preparation of AD-PGA-HSA/MS containing up to 45% of the drug through the formation of this AD-salt complex. This is demonstrated in the comparison of the binding data for AD in Table 20 for (HSA/MS-U and PGA-HSA/MS-U and Table 21 for (HSA/MS-Q and PGA-HSA/MS-Q).

TABLE 20

Amount of Bound AD or Unquenched HSA/MS and PGA-HSA/MS

| Wt % of Added PGA | Wt % of Bound AD |
|---|---|
| 0 | 18 |
| 12 | 33 |
| 16 | 39 |

TABLE 20-continued

| Amount of Bound AD or Unquenched HSA/MS and PGA-HSA/MS | |
|---|---|
| Wt % of Added PGA | Wt % of Bound AD |
| 22 | 46 |

TABLE 21

| Amount of Bound AD for Quenched HSA/MS and PGA-HSA/MS | |
|---|---|
| Wt % of Added PGA | Wt % of Bound AD |
| 0 | 18 |
| 11 | 21 |
| 15 | 25 |
| 19 | 33 |

The data shows that as the concentration of PGA increases in the MS, the wt % of bound AD also increases. This data also shows that the amount of bound AD is higher for the MS-U than the MS-Q at comparable amounts of PGA and is attributable to the increased amount of AD that can be covalently bound to HSA/MS-U than the physically bound AD to HSA/MS-Q.

The ionic AD-salt complex is sensitive to pH. Adjusting the pH directly affected the amount of AD bound to the PGA-HSA/MS-Q. The optimum pH for binding was found to be 6.0 and corresponded to 32 wt % complexed drug.

AD-HSA/MS were mounted in epoxy and serial section with a ultramicrotome, the sections were mounted on TEM grids and examined with an optical microscope. The red chromophor of AD could be seen throughout the slices and indicated that the drug had penetrated into the matrix of the HSA/MS as well as on the surface.

It is a feature of the invention that the hydrophilic nature of HSA/MS allows for the incorporation of therapeutic agents to the albumin/MS after their synthesis. This is inherently different from prior art procedures which add the drugs to the aqueous phase before the dispersion process and the formation of the microspheres. The advantage of drug addition after MS synthesis are: (1) higher drug loadings and (2) ability to bind chemically sensitive drugs that otherwise may be affected during the formation of the MS.

The in vitro AD release rates for AD-albumin/MS were found to be readily controlled and due to the three distinct binding mechanisms of AD to albumin/MS; (1) slow—hydrolytic degradation of covalent bonds, (2) medium—dissociation of the drug salt complex, and (3) fast—release of physically adsorbed drug.

For the unquenched MS (HSA/MS-U and PGA-HSA/MS-U) the amount of AD released in 15 hrs varied from 23% to 50%. Increasing the concentration of PGA in HSA/MS increased the amount of released AD. Since the PGA-AD salt complex dissociates faster than hydrolytic degradation of covalently bound AD, increasing the amount of incorporated PGA increases the rate of AD release. For AD-HSA/MS-Q and AD-PGA/MS-Q, the amount of AD released in 15 hrs varied from 55% to over 80%. As the amount of PGA increases, the percent of the total amount of AD that is released decreases. Since the MS are quenched, the number of reactive aldehydes that are available to covalently bind AD are reduced. The predominate drug binding mechanism would then be by physical association and drug-salt formation. The physically adsorbed AD is released faster than salt dissociation. Therefore, as the amount of the PGA is increased in the MS, a higher percentage of the bound AD is associated with the salt complex. This causes a larger % of the released AD to be by salt dissociation which reduces the release rate. With respect to quenching, glycine would incorporate a higher amount of terminal carboxyl groups than the amino alcohol due to basic structural differences between the two molecules. Higher amounts of free carboxyl groups would allow higher concentrations of AD bound by salt formation. Because the salt complex is stable in water, the MS with the highest concentration of carboxyl groups (AD-PGA-HSA/MS-Q, COOH) would release the lowest amount of AD when water was used as the mobile phase through the dynamic flow column. AD-HSA/MS-Q (OH), would contain the least amount of carboxyl groups (albumin itself contains some of these groups) and therefore would release the highest amount of AD during the water phase. When the mobile phase is exchanged with saline, the salt dissociates releasing AD. Dynamic flow in vitro release rates do not accurately represent kinetic behavior in vivo, only animal models can determine that type of information. It does, however, allow comparisons to be made between drug carriers so that adequate evaluations can be made before expensive laboratory animal models are used. Furthermore, the dynamic column system is, at best, a representation of controlled drug delivery in the blood circulatory system due to the fast continuous flow. In actuality, MS implanted inside a solid tumor would not be subject to such a rapid turnover of fluid. The slow fluid turnover in the tumor can be better represented by a semi-static in vitro release model. In a static system, drug release from AD-HSA/MS would be regulated by the mechanisms described as well as the concentration of released AD in the AD-HSA/MS environment. As the drug is released into the closed system (i.e., tumor mass), a concentration level would be reached where further drug release would be inhibited. Drug seepage out of the tumor area would then reduce the concentration gradient to a point where more drug would then be released from AD-HSA/MS.

In the toxicity study reported above, a dose level of 600 μg of free AD killed over 80% of the animals tested. The same amount of AD now bound to PGA-HSA/MS resulted in no deaths. When AD-PGA-HSA/MS with 1500 g of bound AD were administered i.p., 60% of the mice survived. Another hazard with AD is the severe necrotic lesions that develop at the site of injection when there is drug leakage around the needle. These ulcers can take months to heal. All animals treated with free AD developed these ulcers. No ulcer development was seen with animals injected with the AD containing MS. Control groups consisting of PGA-HSA/MS did not demonstrate any noticeable toxic effects.

An important characteristic of a successful drug implant is the ability of the drug-carrier to biodegrade once implanted and release of the therapeutic agent. Albumin/MS synthesized in this study were examined for these properties. It was found that highly crosslinked FTIC-BSA/MS that were injected into CD-1 mouse muscle tissue started to degrade by the fourth week and remained immobilized at the site of injection. By varying the cross-linking density, variations in the rate of degradation in vivo may be achieved.

AD-HSA/MS were also implanted into CD-1 muscle tissue and examined after tissue removal. The AD molecule has natural fluorescent abilities and could be easily observed with the optical microscope under fluorescent light. Tissue samples observed after four weeks from day of injection still showed the red chromophor of AD in the surrounding tissue next to the immobilized AD-HSA/MS.

This study demonstrates three important characteristics of the albumin/MS produced according to the invention. These are: (1) to remain localized at site of injection, (2) biodegradation after implantation and (3) drug releasing properties after injection.

Preparation of Bleomycin-Albumin/Microspheres

EXAMPLE 37

Bleomycin Sulfate (BLM) was supplied in 10.0 ml sealed glass vials containing between 8 and 9 mg of a lyophilized white powder that was amorphous in texture. To measure the exact concentration of the BLM, the glass vials were opened in the exhaust hood and the drug dissolved by the addition of known volumes of water. The concentration was then determined with the UV/VIS at an adsorbance of 294 nm and using an extinction coefficient of 12.15 ml/mg (Windholz, M., et al, The Merck Index, Merck & Co., Inc. p. 171 (1976)).

EXAMPLE 38

30 wt % Bleomycin-Human Serum Albumin/Microspheres-Unquenched

A stock solution of BLM was prepared containing 66.7 mg BLM in 25.0 ml of water. An aliquot consisting of 5.0 ml of the clear solution (13.3 mg BLM) was combined with 11.3 mg HSA/MS-U (synthesized as described in Example 1) in a screw cap test tube. The pH of the Brown cloudy mixture was adjusted from 4.23 to 5.97 by the addition of 0.1N NaOH and mixed with a rotary mixer in the dark at 4° C. for 7 hrs. BLM-HSA/MS-U were washed free of the unbound BLM and supernate saved for analysis as described above. After the last wash, the MS were dehydrated with acetone and allowed to air dry. The MS product was a brown powder, 11.7 mg, 73% yield containing 30 wt % drug.

In vitro Release

The release of free BLM from BLM/HSA/MS-U (11.7 mg) was performed using the in vitro dynamic flow column described above. See Table 22.

TABLE 22

BLM Release from 29 wt % BLM-HSA/MS-U (29 μm)
11.67 mg BLM-HSA/MS-U (3.50 mg BLM)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 1.29 | 0.06 | 0.04 | 0.03 | 0.02 | 0.02 | 0.01 |
| Cumulative Wt BLM (mg) | 1.29 | 1.35 | 1.39 | 1.42 | 1.44 | 1.46 | 1.47 |
| % Released | 37 | 39 | 40 | 41 | 41 | 42 | 42 |

EXAMPLE 39

31 wt % Bleomycin-Polyglutamic Acid (9%)-Human Serum Albumin/Microspheres-Unquenched An aliquot consisting of 5.0 ml of the BLM stock solution (13.34 mg BLM) prepared as described above was combined with 12.7 mg of PGA (9%)-HSA/MS-U (synthesized as described above) in a screw cap test tube. The pH of the mixture was adjusted from 4.71 to 6.00 by the addition of 0.1N NaOH and mixed at 4° C. in the dark for 7 hrs. The BLM-PGA(9%)-HSA/MS-U were removed from solution and concentration of the bound drug was determined as described above. The product was a brown powder, 13.15 mg, 72% yield. Concentration of the bound drug was 5.69 mg or 31 wt %.

In vitro Release

The in vitro release of free BLM from BLM-PGA(9%)-HSA/MS-U (13.15 mg) was measured as described above. See Table 23.

TABLE 23

BLM Release from 31 wt %
BLM-PGA(9%)-HSA/MS-U (27 μm)
13.15 mg BLM-PGA(9%)-HSA/MS-U (4.08 mg BLM)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 2.32 | 0.09 | 0.06 | 0.03 | 0.04 | 0.02 | 0.0 |
| Cumulative Wt BLM (mg) | 2.32 | 2.41 | 2.47 | 2.50 | 2.54 | 2.56 | 2.56 |
| % Released | 57 | 59 | 61 | 61 | 62 | 63 | 63 |

EXAMPLE 40

30 wt % Bleomycin-Polyglutamic Acid (14%)-Human Serum Albumin/Microspheres-Unquenched An aliquot consisting of 5.0 ml of the stock BLM solution (13.34 mg BLM) prepared as above was combined with 12.8 mg of PGA(14%)-HSA/MS-U (synthesized as described above) in a screw cap test tube. The pH of the cloudy mixture was adjusted from 4.83 to 6.00 by the addition of 0.1N NaOH and mixed with a rotary mixer at 4° C. in the dark for 7 hrs. BLM-PGA(14%)-HSA/MS-U were washed out of the free drug solution, dehydrated and concentration of the bound drug was determined as described in Example 38. The product was a brown powder, 13.8 mg, 75% yield. Concentration of the bound BLM was 5.56 mg or 30 wt %.

In vitro Release

The in vitro release of the free BLM from BLM-PGA(14%)-HSA/MS-U (13.8 mg) was measured as described above. See Table 24.

TABLE 24

BLM Release from 30 wt %
BLM-PGA(14%)-HSA/MS U (31 μm)
13.8 mg BLM-PGA(14%)-HSA/MS-U (4.14 mg BLM)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 2.41 | 0.06 | 0.03 | 0.02 | 0.02 | 0.01 | 0.01 |
| Cumulative Wt BLM (mg) | 2.41 | 2.47 | 2.50 | 2.52 | 2.54 | 2.55 | 2.56 |
| % Released | 58 | 60 | 60 | 61 | 61 | 62 | 62 |

EXAMPLE 41

23 wt % Bleomycin-Human Serum Albumin/Microspheres-Quenched

A stock solution of BLM was prepared containing 62.7 mg dissolved with 25.0 ml of water in a volumetric flask. An aliquot consisting of 5.0 ml (12.54 mg) was combined with 11.9 mg of HSA/MS-Q in a screw cap test tube. The pH of the mixture was adjusted from 3.95 to 5.95 by the addition of 1.0N NaOH and mixed with a rotary mixer at 4° C. in the dark for 19 hrs. The BLM-HSA/MS-Q were removed from solution, dehydrated and concentration of bound drug was determined as described above. The product was a brown powder, 11.8 mg, 76% yield. Concentration of the bound drug was 3.58 mg or 23 wt %.

In vitro Release

The in vitro release of the free BLM from BLM-HSA/MS-Q (11.81 mg) was measured and the results set forth in Table 25.

TABLE 25

| | BLM Release from 23 wt % BLM-HSA/MS-Q (29 μm) 11.81 mg BLM-HSA/MS-Q (2.71 mg) | | | | | | |
|---|---|---|---|---|---|---|---|
| | Time (hrs) | | | | | | |
| Drug Release | 2.0 | 4.0 | 6.0 | 8.0 | 10.0 | 12.0 | 14.0 |
| Wt BLM (mg) | 1.16 | 0.04 | 0.02 | 0.02 | 0.01 | 0.0 | 0.0 |
| Cumulative Wt BLM (mg) | 1.16 | 1.20 | 1.22 | 1.24 | 1.25 | 1.25 | 1.25 |
| % Released | 43 | 44 | 45 | 46 | 46 | 46 | 46 |

EXAMPLE 42

20 wt % Bleomycin-Polyglutamic Acid(9%)-Human Serum Albumin/Microspheres-Quenched An aliquot consisting of 5.0 ml of the stock BLM solution (12.54 mg BLM) was combined with 13.9 mg of PGA(9%)-HSA/MS-Q in a screw cap test tube. The pH of the mixture was adjusted from 3.68 to 5.98 by the addition of 0.1N NaOH and mixed with a rotary mixer at 4° C. in the dark for 19 hrs. The BLM-PGA(9%)-HSA/MS were washed out of the free BLM solution, dehydrated and concentrations of the bound drug was determined as described above. The product was a brown powder, 16.2 mg, 84% yield. Concentration of the bound drug was 5.51 mg or 28 wt %.

In vitro Release

The release of the free BLM from BLM-PGA(9%)-HSA/MS-Q (16.20 mg) was measured and the results are set forth in Table 26.

TABLE 26

| | BLM Release from 28 wt % BLM-PGA(9%)-HSA/MS-Q (27 μm) 16.20 mg BLM-PGA(9%)-HSA/MS-Q (4.54 mg BLM) | | | | | | |
|---|---|---|---|---|---|---|---|
| | Time (hrs) | | | | | | |
| Drug Release | 2.0 | 4.0 | 6.0 | 8.0 | 10.0 | 12.0 | 14.0 |
| Wt BLM (mg) | 2.53 | 0.05 | 0.02 | 0.01 | 0.01 | 0.0 | 0.0 |
| Cumulative Wt BLM (mg) | 2.53 | 2.58 | 2.60 | 2.61 | 2.62 | 2.62 | 2.62 |
| % Released | 56 | 57 | 57 | 57 | 58 | 58 | 58 |

EXAMPLE 43

29 wt % Bleomycin-Polyglutamic Acid (14%)-Human Serum Albumin/Microspheres-Quenched An aliquot consisting of 5.0 ml of the stock BLM solution (12.54 mg BLM) was combined with 12.1 mg of PGA(14%)-HSA/MS-Q in a screw cap test tube. The pH of the mixture was adjusted from 3.65 to 5.97 by the addition of 0.1N NaOH and mixed with a rotary mixer at 4° C. in the dark for 19 hrs. The BLM-PGA(14%)-HSA/MS-Q were washed out of the free BLM solution, dehydrated and concentration of the bound drug was determined as described above. The product was a brown powder, 13.2 mg, 78% yield. Concentration of the bound drug was 4.98 mg or 29 wt %.

In vitro Release

The release of the free BLM from BLM-PGA(14%)-HSA/MS-Q (13.21 mg) was measured and release results are set forth in Table 27.

TABLE 27

| | BLM Release from 29 wt % BLM-PGA(14%)-HSA/MS-Q (31 μm) 13.21 mg BLM-PGA(14%)-HSA/MS-Q (3.83 mg BLM) | | | | | | |
|---|---|---|---|---|---|---|---|
| | Time (hrs) | | | | | | |
| Drug Release | 2.0 | 4.0 | 6.0 | 8.0 | 10.0 | 12.0 | 14.0 |
| Wt BLM (mg) | 2.15 | 0.04 | 0.02 | 0.01 | 0.0 | 0.0 | 0.0 |
| Cumulative Wt BLM (mg) | 2.15 | 2.19 | 2.21 | 2.22 | 2.22 | 2.22 | 2.22 |
| % Released | 56 | 57 | 58 | 58 | 58 | 58 | 58 |

EXAMPLE 44

12 wt % Gentamycin-Human Serum Albumin/Microspheres-Unquenched

A solution of GMC (gentamycin sulfate) was prepared containing 257.9 mg dissolved with 25.0 ml of water in volumetric flask. An aliquot consisting of 5.0 ml of the clear solution (51.58 mg) was combined with 50.5 mg of the dehydrated HSA/MS-U (synthesized as described in Example 1 in a screw cap test tube. The pH of the brown cloudy mixture was adjusted from 5.18 to 5.70 by the addition of 0.1N NaOH and mixed at 4° C. in the dark for 12 hrs. GMC-HSA/MS-U were washed free of the unbound GMC and supernate saved for analysis as described above. After the last wash, the MS were dehydrated with acetone and allowed to air dry. The MS product was a brown powder, 52.4 mg, 92% yield containing 12 wt % drug.

Gentamycin sulfate (GMC) has an aminoglycoside structure with no detectable absorbance in either the ultraviolet or visable range. In order to quantitate the concentration of GMC for the drug binding experiments, a modification of the Barends et al [A. J. Chromatography, Vol. 222, pg. 316 (1981)] procedure was used.

EXAMPLE 45

16 wt % Gentamycin-Polyglutamic Acid(17%)-Human Serum Albumin/Microspheres-Unquenched A solution of GMC was prepared containing 252.02 mg dissolved in 25.0 ml of water in a volumetric flask. An aliquot consisting of 10.0 ml of the clear solution (100.81 mg) was combined with 119.06 mg of PGA(17%)-HSA/MS-U in a screw cap test tube. The pH of the brown cloudy mixture was adjusted from 5.30 to 5.74 by the addition of 0.1N NaOH and mixed with a rotary mixer at 4° C. in the dark for 12 hrs. GMC-PGA(17%)-HSA/MS-U were removed from the free drug solution by centrifugation, washed and dehydrated as described above. The supernate was saved for analysis. The MS product was a brown powder, 113.6 mg, 81% yield.

EXAMPLE 46

15 wt % Gentamycin-Polyglutamic Acid(19%)-Bovine Serum Albumin/Microspheres-Unquenched A solution of GMC was prepared containing 252.94 mg dissolved in 25.0 ml of water in a volumetric flask.

An aliquot consisting of 10.0 ml of the clear solution (101.18 mg GMC) was combined with 127.72 mg of the dehydrated PGA(19%)-BSA/MS-U in a screw cap test tube. The pH of the brown cloudy mixture was adjusted from 5.12 to 5.83 by the addition of 0.1N NaOH and mixed with a rotary mixer at 4° C. in the dark for 12 hrs. GMC-PGA(19%)-BSA/MS-U were removed from the free drug solution by centrifugation washed and dehydrated as described above.

In vitro Release

The in vitro release of GMC from GMC-PGA(19%)-BSA/MS-U was performed as described above. Concentration of the free drug in the collected fractions was analyzed as described in Example 44. Release data is set forth in Table 28.

TABLE 28

| GMC Release from 18 wt % GMC-PGA(19%)-BSA/MS-U (18 μm) 16.37 mg GMC-PGA(19%)-BSA/MS-U (246 mg GMC) | | | | | | | |
|---|---|---|---|---|---|---|---|
| | Time (hrs) | | | | | | |
| Drug Release | 2.0 | 4.0 | 6.0 | 8.0 | 10.0 | 12.0 | 14.0 |
| Wt GMC (mg) | 1.66 | 0.40 | 0.16 | 0.01 | 0.0 | 0.0 | 0.0 |
| Cumulative Wt GMC (mg) | 1.66 | 2.15 | 2.31 | 2.32 | 2.32 | 2.32 | 2.32 |
| % Released | 66 | 86 | 94 | 95 | 95 | 95 | 95 |

EXAMPLE 47

18 wt % Streptomycin-Polyglutamic Acid(14%)-Bovine Serum Albumin/Microspheres-Unquenched STM (259.6 mg) was dissolved with 25.0 ml of water, 5.0 ml of the clear solution (51.92 mg STM) was combined with 48.3 mg of PGA(14%)-BSA/MS-U prepared as described in Example 24 in a screw cap test tube. The pH of the cloudy white mixture was adjusted from 4.23 to 5.79 by the addition of 0.1N NaOH and mixed with a rotary mixer at 4° C. in the dark for 18 hrs. The mixture was centrifuged (200 RPM×2 mins) and the clear supernate was removed and saved for analysis. The STM-PGA(14%)-BSA/MS-U were removed from the free drug solution, washed and dehydrated. The MS product was a white powder, 27.5 mg, 47% yield.

Streptomycin sulfate (STM) has no detectable absorbance in either the ultraviolet or visable range. As with GMC, STM has to be modified in order to quantitate the amounts of STM bound STM to the MS. The manitol procedure by Grove and Randall in *Assay Methods of Antibiotics a Laboratory Manual*, Welch, H, and Martin Ibaneze, F, eds. Medical Encyclopedia, Inc., New York, N.Y., p. 34 (1975) was used.

EXAMPLE 48

23 wt % Streptomycin-Polyglutamic Acid(14%)-Bovine Serum Albumin/Microspheres-Quenched A volume of 5.0 ml of the stock STM solution (51.92 mg STM) was combined with 38.8 mg of the PGA(14%)-BSA-PGA/MS-Q prepared as described in Example 22 in a screw cap test tube. The pH of the cloudy white mixture was adjusted from 4.32 to 5.86 by the addition of 0.1N NaOH and mixed with a rotary mixer in the dark for 4° C. for 18 hrs. The STM-PGA(14%)-BSA/MS-Q were removed from the free drug solution and the bound STM was determined as described above. The product was a white powder, 34.8 mg, 70% yield. Concentration of bound STM was 11.28 mg or 23 wt %.

EXAMPLE 49

12 wt % Streptomycin-Polyglutamic Acid(14%)-Bovine Serum Albumin/Microspheres-Quenched and Lyophilized A volume of 5.0 ml of the stock STM solution (51.92 mg STM) was combined with 39.7 mg of lyophilized PGA(14%)-BSA/MS-Q in a screw cap test tube. The pH of the cloudy white mixture was adjusted from 4.47 to 5.80 by the addition of 0.1N NaOH and mixed with a rotary mixer in the dark at 4° C. for 18 hrs. STM-PGA(14%)-HSA/MS-Q were washed out of the free STM solution, and concentration of the bound drug was 5.63 mg or 12 wt %.

EXAMPLE 50

13 wt % Streptomycin-Polyglutamic Acid(14%)-Bovine Serum Albumin/Microspheres-Quenched (Wet)

A volume of 5.0 ml of the stock STM solution (51.92 mg STM) was combined with 3.0 ml of PGA(14%)-BSA/MS-Q (9.7 mg/ml) or 29.4 mg total MS, suspended in 3.0 ml of water, in a screw cap test tube. The combination of the two solutions (STM and MS) produced a final volume of 8.0 ml. The pH of the cloudy white mixture was adjusted from 5.10 to 5.91 by the addition of 0.1N NaOH and mixed with a rotary mixer in the dark at 4° C. for 18 hrs. STM-PGA(14%)-BSA/MS-Q were washed out of the free drug solution, and concentration of the bound drug was 4.39 mg or 13 wt %.

EXAMPLE 51

23 wt % Streptomycin-Carboxymethylkdextran(12%)-Bovine Serum Albumin/Microspheres-Quenched STM (255.2 mg) was dissolved in 25.0 ml of water, 5.0 ml of the clear solution (51.04 mg STM) was combined with 58.4 mg of CMD(12%)-BSA/MS-Q in a screw cap test tube. The pH of the cloudy white mixture was adjusted from 3.35 to 5.90 by the addition of 0.1N NaOH and mixed with a rotary mixer at 4° C. in the dark for 18 hrs. MS were washed out of the free drug solution, dehydrated and concentration of the bound STM was determined. The product was a white powder, 60.3 mg, 85% yield. Concentration of the bound drug was 23 wt %.

EXAMPLE 52

Magnetically responsive albumin microspheres were prepared as follows: Human serum albumin, 576 mg, and 21% magnetite in 0.1% bovine serum albumin in phosphate buffered saline (BSA-PBS), 114 mg, was dissolved in 1.9 ml distilled water at 23° C. and added to 1% solution of cellulose acetate butyrate in dichloroethane (50 ml). The albumin-magnetite solution was dispersed with a 20 KHz sonicator at 375 w for 10 minutes in a ice bath. Glutaraldehyde in toluene was used for cross-linking. Aqueous glutaraldehyde (25% biological grade), 10 ml, and toluene, 40 ml, were combined in a test tube and dispersed by sonication. After allowing the two phases to separate, the resulting solution of glutaraldehyde was added to another 1% solution of cellulose acetate butyrate in dichloroethane, 110 ml, in a round bottom flask. While stirring at 1500 rpm with an overhead stirrer, at room temperature, the albumin-magnetite dispersion was added and stirred for 2 hours. Cross-linking was completed by gently mixing for 18 hours at room temperature. The cross-linked HSA/MS were washed several times by suspending in acetone and centrifuging at 50,000 G for 30 minutes. The washed MS were then suspended in water and centrifuged at 1,500 G for 15 minutes the supernatant was discarded and the pellet stored in distilled water at room temperature. The MS produced were magnetically responsive and hydrophilic. The diameter of the microspheres were not larger than 200 nanometers, and had a number average diameter of 80 nanometers with a magnetite concentration of 4% by weight. The MS product was a brown suspension, 0.490 g dry weight, 82% yield.

EXAMPLE 53

Human serum albumin, 190 mg, polyglutamic acid, 60 mg, and 21% magnetite in 0.1% BSA-PBS, 240 mg, were dissolved in 0.8 ml distilled water at 23° C. and added to 2% cellulose acetate in dichloroethane (20 ml). The albumin-magnetite solution was dispersed with a vortex mixer at maximum power for 10 minutes. The glutaraldehyde solution as previously described (5 ml) was added and mixed for 18 hours at room temperature. The cross-linked MS were washed several times with acetone and the free reactive aldehyde groups were quenched by suspending in 1M glycine (10 ml/100 mg MS) and mixed for 18 hours. The MS were washed several times in distilled water, several times in acetone, and air dried. The microspheres produced were magnetically responsive hydrophilic HSA/MS containing 20% magnetite and 24% polyglutamic acid, by weight, and with an average diameter of between 1–10 microns. The MS product was a dark powder, 0.288 g, 96% yield. Primaquine (100 mg), was dissolved in 50.0 ml of water in a volumetric flask. A volume consisting of 5 ml of the clear yellow solution 10 mg) was combined with 10.0 mg of the HSA/MS (that were synthesized in this example) in a screw cap test tube. The pH of the cloudy orange mixture was adjusted to 6.1 and mixed gently for 18 hours at 4° C. The MS were washed several times with distilled water, air dried and stored dry at 4° C. The MS contained 24% primaquine by weight.

EXAMPLE 54

Human serum albumin, 0.780 g, polyglutamic acid, 0.200 g, and 21% magnetite in 0.1% BSA-PBS, 95 mg, was dissolved in 3.3 ml distilled water at 23° C. and added to 1% CAB in dichloroethane (50 ml). The albumin-magnetite solution was dispersed and cross-linked with a solution consisting of 110 ml of 1% CAB and 50 ml of the glutaraldehyde solution described previously in Example 52. The cross-linked MS were washed several times with acetone and water. The albumin MS produced were magnetically responsive and hydrophilic, they contained 20% polyglutamic acid and 2% magnetite by weight. Average diameter of the MS produced in this example was 80 nanometers. The MS product was a brown suspension, 0.537 g dry weight, 54% yield. Adriamycin, 10 mg, was dissolved in 5 ml of distilled water and mixed with 10 mg of the MS product. The pH was adjusted to 7.0 and 0.5N NaOH and the red cloudy solution was then mixed for 18 hours in the dark at 4° C. The microspheres contained 50% of the drug by weight and were washed then stored in distilled water.

EXAMPLE 55

Human serum albumin, 830 mg, 21% magnetite in 0.1% BSA-PBS, 720 mg, and BaSO4, 20 mg, was dissolved in 2.7 ml distilled water at 23° C. and added to 2% CEB in dichloroethane (35 ml). The albumin-magnetite mixture was dispersed with a vortex mixer at maximum power for 10 minutes. The glutaraldehyde solution described previously (10 ml) was added and mixed gently for 18 hours at room temperature. The cross-linked microspheres were washed several times with acetone and air dried. The microspheres produced were magnetically responsive and hydrophilic that contained 15% magnetite and 2% BaSO4, by weight with an average diameter of between 1–10 microns. The MS product was a dark brown powder, 0.960 g, 95% yield.

The magnetically responsive microspheres of the present invention, unlike those of the prior art are hydrophilic and may be readily dispersed in aqueous media for injection without the need for surfactants. In addition, they may be readily prepared with the incorporation of very high concentrations of therapeutic agents such as the cancer chemotherapeutic drug adriamycin (up to 50 wt % drug). Previous magnetically responsive hydrophobic albumin microsphere-drug preparations have usually succeeded in incorporating not more than 10–15 wt % of such anti-tumor drugs. Also, the hydrophobic magnetically responsive albumin microsphere preparations known in the art have been compromised by a larger dispersion of sizes, limiting the smallest practical size to $\mu$m. In contrast, the method of the present invention enables the preparation of particles as small as 80 nm with a narrow distribution of size.

Using a polypeptide cross-linking agent such as glutaraldehyde, reactive aldehyde groups are available on the microspheres for additional chemical reaction. The microspheres may be reacted with amino group containing drugs for covalent coupling, or with the amino acid glycine to enhance hydrophilicity, or coupled covalently to such large protein molecules as lectins, enzymes or antibodies to modify the microsphere surface properties or to provide a carrier system for the coupled proteins. Coupling antibodies to the magnetically responsive microspheres provides methods for the selective removal of cells from cell cultures in suspension by targeting the microspheres to the surface of specific cells, rendering them magnetic, and pulling the cell-microsphere conjugate from solution by means of an externally applied magnetic field, or for use in vivo as a diagnostic aid. Antibodies coupled to magnetically responsive submicron microspheres applied in vivo, i.e., injected intra-arterially, intra-veinously, intra-lymphatically, etc., may localize the microspheres on the surface of specific cells providing a radiopaque element for either radiographic imaging or, magnetic resonance imaging. One type of magnetically responsive microspheres currently used for separation of cell culture suspensions are made of polystyrene which gives a relatively unreactive surface to which antibodies can only be coupled by passive adsorption. As a result, the antibodies tend to dissociate from the microsphere surface with time, necessitating the use of excessive amounts of antibodies and limiting the useful storage life of the microsphere.

The present invention enables the incorporation into the magnetically responsive hydrophilic microspheres of various drugs for localization by means of an extracorporeally applied magnetic field and controlled release, radiographic and magnetic resonance imaging, and selective separation of cell culture suspensions. Various synthetic drugs or enzymes or antibodies or proteins may be incorporated into the microsphere by physical association, by electrostatic interactions, or covalently for altering release kinetics and other property modifications. Such microspheres may also be used for adjuvant compositions incorporating such immunostimulants as interferon or MDP. Albumin may also be combined with various other macromolecules or polypeptides in the course of preparation of the microsphere. For example, polyglutamic acid has been incorporated into magnetically responsive HSA microspheres to enhance the anionic nature of the microsphere and so facilitate the binding of high concentrations of cationic drugs such as adriamycin, bleomycin, or streptomycin. The drugs which may be used in such microspheres include the clinically important antitumor drugs (e.g., adriamycin, mitomycin, bleomycin, etc.) as well as hormones such as cortisone derivatives and antibiotics such as gentamycin, streptomycin, penicillin, etc.

The hydrophilic magnetically targeted drug containing microspheres of the invention offer opportunities for new methods of drug delivery and greater safety for immunotherapy, chemotherapy, hormone therapy, antibiotic therapy, in both human and veterinary applications. Additionally, the microspheres of the invention find applications in new magnetic resonance imaging and radiological diagnostic techniques, and for highly specific cell separations.

EXAMPLE 56

A batch was prepared as follows: HSA 0.6 was dissolved in 2.0 ml distilled water and added to 1% solution of cellulose acetate butyrate (CAB) in dichloroethane (50 ml). The albumin solution was dispersed with 20 Khz sonicator at 375 W for 10 minutes in an ice bath. A 40 ml glutaraldehyde saturated toluene solution (see Example 1) was combined in a round bottom flask with 110 ml 1% CAB. While stirring at 1500 rpm at room temperature, the albumin dispersion was added and stirred for 2 hours. Cross-linking was completed by gently mixing for 18 hours at room temperature. The cross-linked HSA/MS were washed several times by suspending in acetone and centrifuging at 50,000 G for 30 minutes. The washed MS were then suspended in 95% ethyl alcohol and centrifuged at 50,000 G for 30 minutes and the pellet resuspended and stored at 4° C. in distilled water. The MS produced were hydrophilic and had a diameter not larger than 200 nonometers, with a number average diameter of 80 nanometers. The MS product was a brown suspension, 0.306 g dry weight, 51% yield.

We claim:

1. A method of preparing novel hydrophilic, magnetically responsive microspheres consisting essentially of cross-linked protein or polypeptide particulate and a magnetically responsive material comprising
  (a) providing a dispersion of an aqueous solution or dispersion of polypeptide or protein microspheres and a particulate magnetically responsive material in an organic, substantially water immiscible solvent solution of a high molecular weight polymer, said organic solvent being substantially a non-solvent for said microspheres and said polymer solution stabilizing the dispersion of microspheres and magnetically responsive material,
  (b) incorporating a polyfunctional cross-linking agent for said protein or polypeptide in said dispersion, and
  (c) allowing said cross-linking agent to react with said protein or polypeptide microspheres for a time sufficient to cross-link at least a portion of the microspheres, thereby providing magnetically responsive microspheres containing free reactive functional groups.

2. The method of claim 1 including the step of separating said cross-linked protein or polypeptide microspheres from said dispersion.

3. The method of claim 1 wherein said protein is albumin.

4. The method of claim 3 wherein said albumin is human serum albumin.

5. The method of claim 3 wherein said albumin is bovine serum albumin.

6. The method of claim 1 or 2 wherein said organic solvent solution of high molecular weight polymer is a solution of polymethylmethacrylate in a mixture of toluene and chloroform.

7. The method of claim 1 or 2 wherein said organic solvent solution of high molecular weight polymer is a solution of polyoxyethylene-polyoxypropylene copolymer in chloroform.

8. The method of claim 1 or 2 wherein said organic solvent solution of high molecular weight polymer is a solution of cellulose acetate butyrate in ethylene dichloride.

9. The method of claim 1 or 2 wherein said organic solvent solution of high molecular weight polymer is a solution of bisphenol polycarbonate in chloroform.

10. The method of claim 1 or 2 wherein the concentrations of high molecular weight polymer in organic solvent is from about 1% to about 40%, by weight.

11. The method of claim 1 or 2 wherein said stabilized dispersion of protein or polypeptide microspheres is formed by dispersing an aqueous solution of said protein or polypeptide in said organic solvent solution of high molecular weight polymer.

12. The method of claim 1 or 2 wherein said microspheres have an average size in the range of from about 0.05 microns to about 500 microns.

13. The method of claim 1 or 2 wherein said cross-linking agent is a dialdehyde.

14. The method of claim 13 wherein said cross-linking agent is glutaraldehyde.

15. The method of claim 1 or 2 wherein said cross-linking agent is a diisocyanate.

16. The method of claim 15 wherein said diisocyanate is 2,4-tolylene diisocyanate or 1,6-diisocyanate hexane.

17. The method of claim 1 wherein said magnetically responsive material is magnetite.

18. The product produced according to the method of claim 1 or 2.

19. The product produced according to the method of claim 3.

20. The method of claim 1 including the step of reacting reactive functional groups of said cross-linked microspheres with a first substance containing at least one functional group reactive therewith to form a covalent bond between said cross-linked microspheres and said substance.

21. The method of claim 20 wherein said first substance is a biologically active substance suitable for administration to a biological system.

22. The method of claim 20 wherein said substance contains at least one additional functional group which is non-reactive with the reactive functional groups of said cross-linked microspheres.

23. The method of claim 22 wherein said at least one additional functional group is reacted with a second substance containing a functional group reactive therewith to form a bond therebetween.

24. The method of claim 23 wherein said second substance is a biologically active substance suitable for administration to a biological system.

25. The method of claim 20 wherein said magnetically responsive material is magnetite.

26. The product produced according to the method of claim 20.

27. The product produced according to the method of claim 21.

28. The product produced according to the method of claim 22.

29. The product produced according to the method of claim 23.

30. The product produced according to the method of claim 24.

31. The product produced according to the method of claim 25.

32. A composition in unit dosage form adapted for administration to a biological system comprising a biologically effective amount of the product of any of claims 26 to 31 and a biologically acceptable carrier therefor.

33. A method of administering a biologically active substance to a biological system comprising administering thereto the product of any of claims 26 to 31.

* * * * *